(12) United States Patent
Ono et al.

(10) Patent No.: US 11,173,076 B2
(45) Date of Patent: Nov. 16, 2021

(54) STRETCHABLE STRUCTURE OF ABSORBENT ARTICLE AND MANUFACTURING METHOD OF THE SAME

(71) Applicant: DAIO PAPER CORPORATION, Ehime (JP)

(72) Inventors: Yohei Ono, Ehime (JP); Yasuko Ishikawa, Ehime (JP)

(73) Assignee: DAIO PAPER CORPORATION, Ehime (JP)

( * ) Notice: Subject to any disclaimer, the term of this patent is extended or adjusted under 35 U.S.C. 154(b) by 617 days.

(21) Appl. No.: 16/088,237

(22) PCT Filed: Feb. 23, 2017

(86) PCT No.: PCT/JP2017/006708
§ 371 (c)(1),
(2) Date: Sep. 25, 2018

(87) PCT Pub. No.: WO2017/169338
PCT Pub. Date: Oct. 5, 2017

(65) Prior Publication Data
US 2020/0397622 A1 Dec. 24, 2020

(30) Foreign Application Priority Data
Mar. 30, 2016 (JP) .............................. JP2016-069153

(51) Int. Cl.
*A61F 13/49* (2006.01)
*A61F 13/496* (2006.01)
*A61F 13/15* (2006.01)

(52) U.S. Cl.
CPC ........ *A61F 13/4902* (2013.01); *A61F 13/496* (2013.01); *A61F 2013/15878* (2013.01); *A61F 2013/49022* (2013.01)

(58) Field of Classification Search
CPC .......... A61F 13/15739; A61F 13/49011; A61F 13/49012; A61F 13/49019; A61F 13/496;
(Continued)

(56) References Cited

U.S. PATENT DOCUMENTS 7,211,531 B2 * 5/2007 Schneider ......... A61F 13/15593
442/328
9,144,522 B2 * 9/2015 Ostertag ........... A61F 13/49011
(Continued)

FOREIGN PATENT DOCUMENTS

JP 2010284229 A 12/2010
JP 2014198178 A 10/2014
(Continued)

OTHER PUBLICATIONS

European Search Report for EP 17773883 dated Aug. 14, 2019.
International Search Report for PCT/JP2017/006708, dated May 30, 2017.

*Primary Examiner* — Michele M Kidwell
(74) *Attorney, Agent, or Firm* — Andrus Intellectual Property Law, LLP

(57) ABSTRACT

A stretchable structure of an absorbent article has a first sheet layer made of a nonwoven fabric; a second sheet layer made of a nonwoven fabric and opposed to one side surface of the first sheet layer; and a plurality of elongated elastically stretchable members provided along the stretchable direction at intervals from each other between the first sheet layer and the second sheet layer. The first sheet layer and the second sheet layer have sheet bonded portions bonded via a hot melt adhesive disposed in a striped pattern that is intermittent in the longitudinal direction of the elastically stretchable members and continuously elongated in the direction intersecting with the elastically stretchable members, and either one of the first sheet layer and the second sheet layer is made of a low-adhesion nonwoven fabric having lower peel strength with respect to the hot melt adhesive than the other sheet layer.

15 Claims, 26 Drawing Sheets

(58) Field of Classification Search
CPC ........... A61F 2013/15569; B29C 65/18; B29C 65/4815; B29C 65/524; B29C 65/526; B29C 65/7435; B29C 65/7437; B29C 65/7441; B29C 65/8215; B29C 65/8223; B29C 66/1122; B29C 66/433; B29C 66/729; B29C 66/7294; B29C 66/83411; B29C 66/83413; B29C 66/83415; B29C 66/83511; B29C 66/8432; B29K 2995/0046; B29L 2031/4878; B32B 2555/02; B32B 5/022; B32B 5/26; B32B 7/12

See application file for complete search history.

(56) References Cited

U.S. PATENT DOCUMENTS

| | | | |
|---|---|---|---|
| 2003/0064652 A1* | 4/2003 | Heden | B29C 66/438 442/382 |
| 2004/0006324 A1* | 1/2004 | Zhou | A61F 13/49014 604/385.24 |
| 2010/0262102 A1 | 10/2010 | Turner et al. | |
| 2012/0083178 A1* | 4/2012 | Sabbagh | B32B 5/022 442/105 |
| 2016/0067115 A1 | 3/2016 | Ishikawa et al. | |
| 2016/0106601 A1 | 4/2016 | Kobayashi et al. | |
| 2019/0021916 A1* | 1/2019 | Ishikawa | B29C 66/83415 |
| 2020/0297552 A1* | 9/2020 | Ono | A61F 13/15593 |
| 2020/0352792 A1* | 11/2020 | Ishikawa | A61F 13/49011 |

FOREIGN PATENT DOCUMENTS

| | | |
|---|---|---|
| JP | 2014-221097 | 11/2014 |
| JP | 2014207973 A | 11/2014 |
| JP | 2015066008 A | 4/2015 |
| KR | 2016-0008528 | 1/2016 |
| WO | 2015041928 | 3/2015 |

* cited by examiner

Fig. 11
(a)
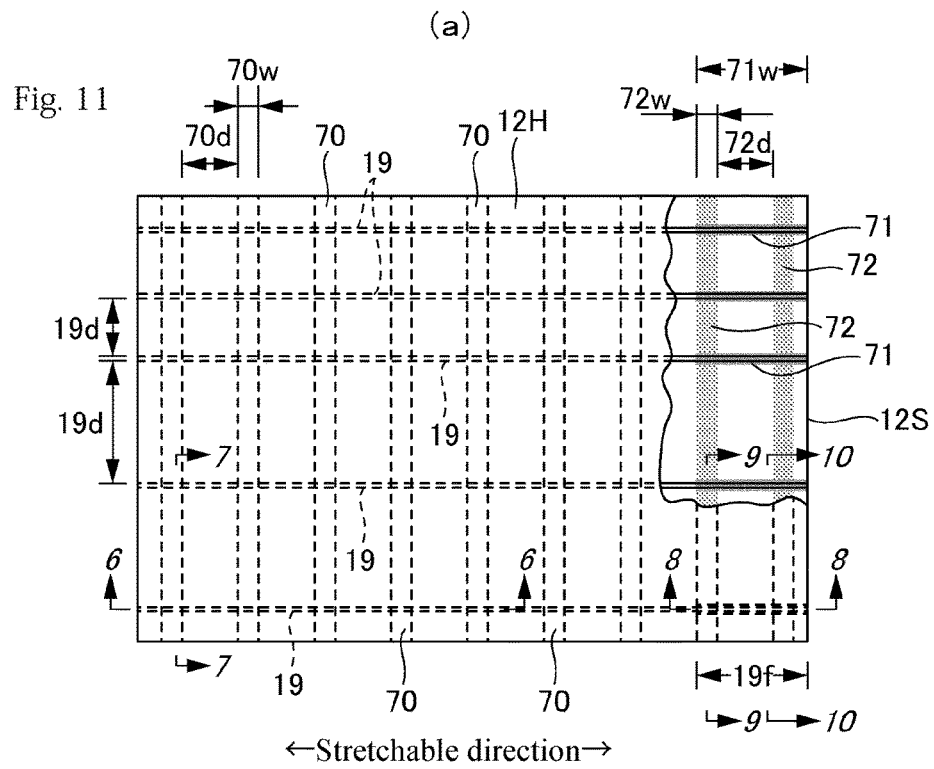
←Stretchable direction→
(b)
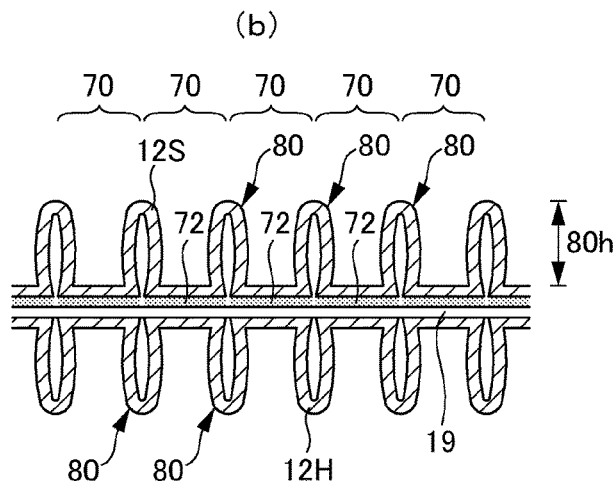
(c)
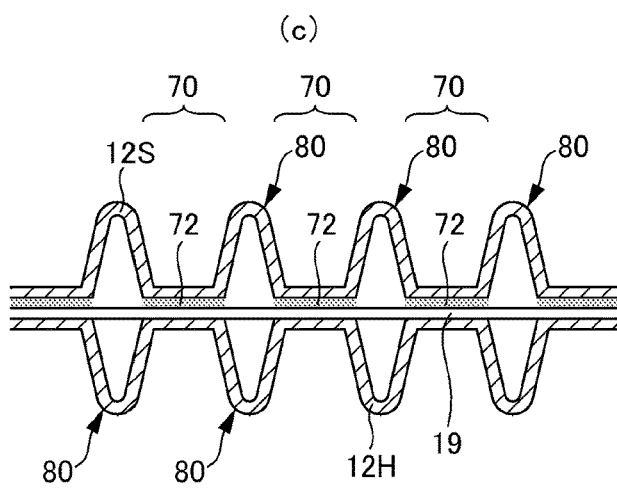

Fig. 12
(d)
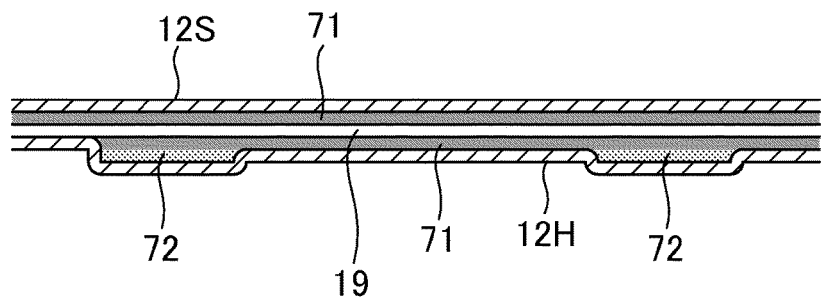
(e)
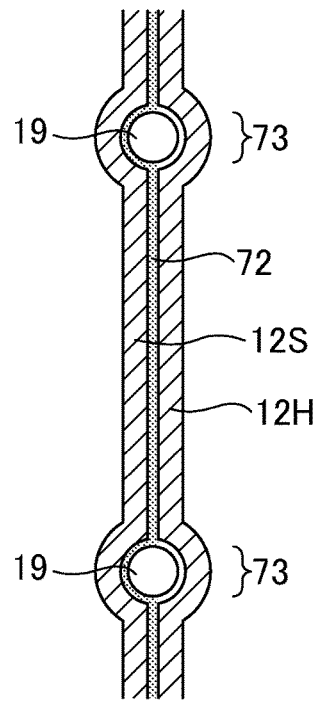
(f)
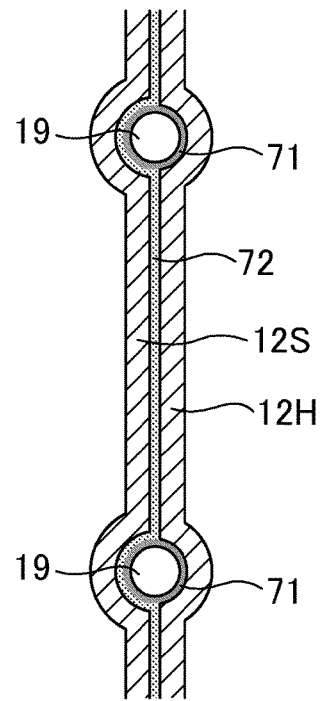
(g)
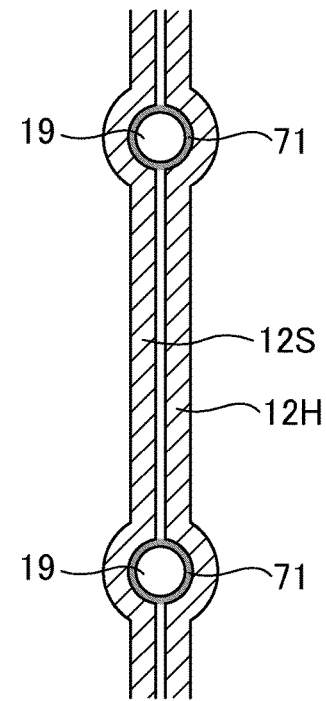

Fig. 13
(a)
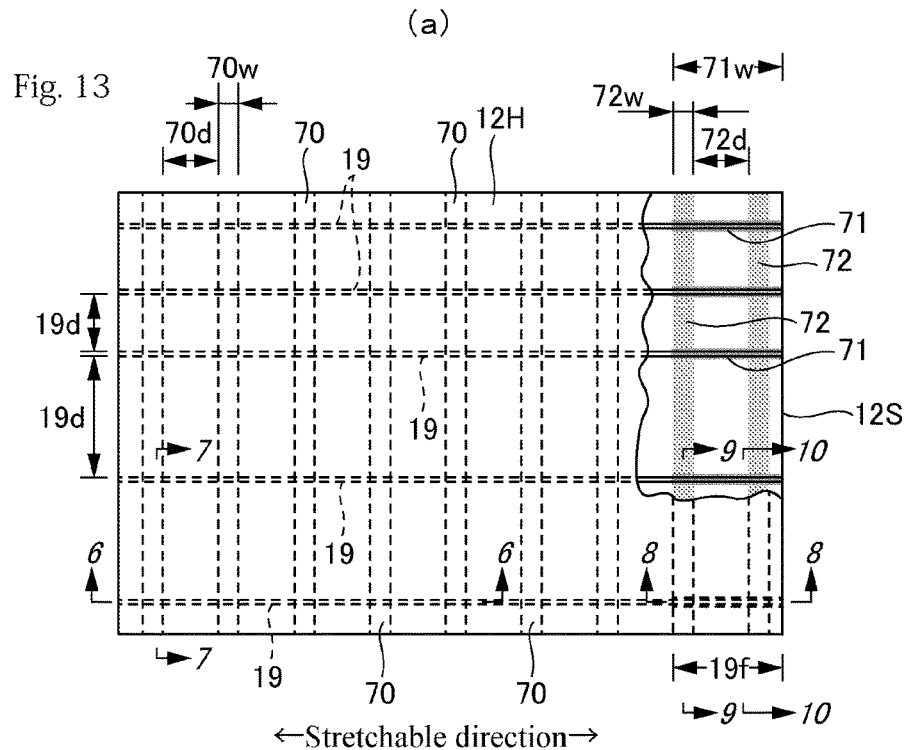
←Stretchable direction→
(b)
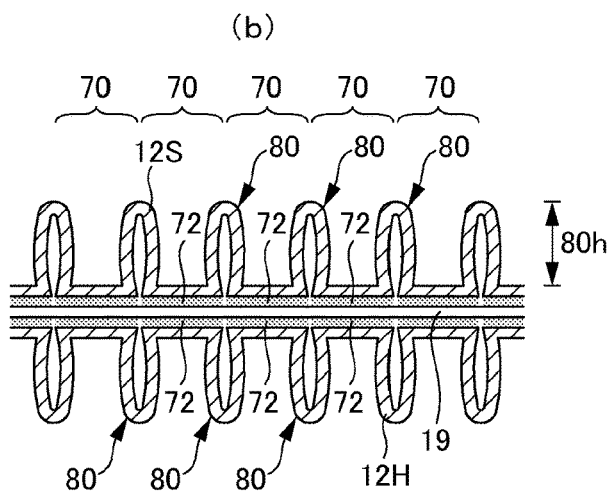
(c)
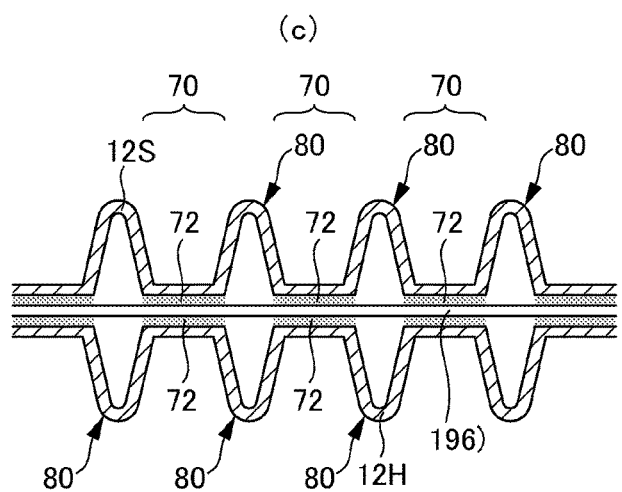

Fig. 14
(d)
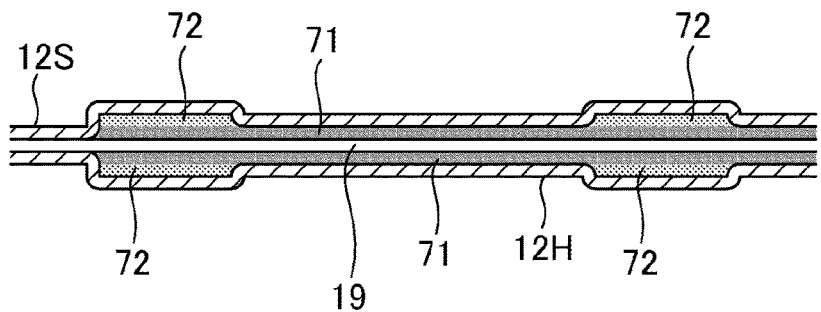
(e) 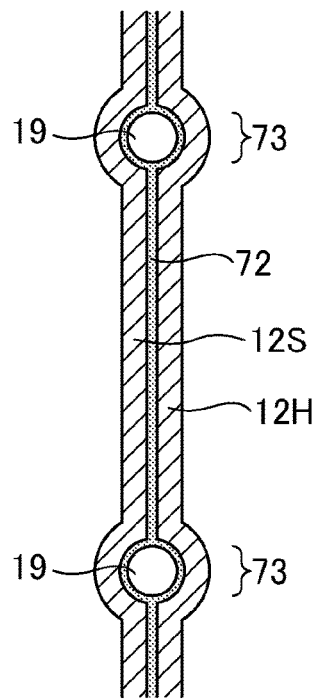
(f) 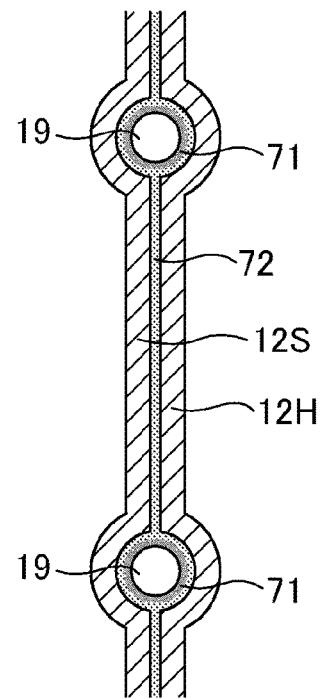
(g) 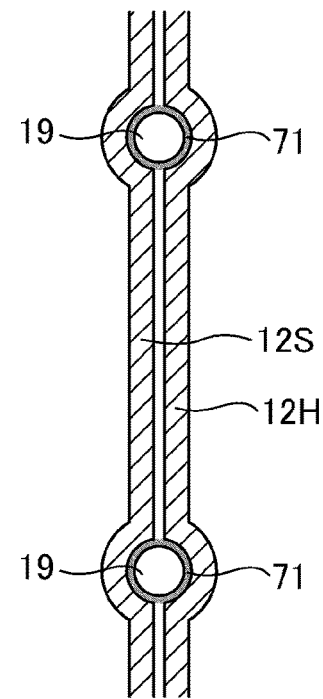

(a)
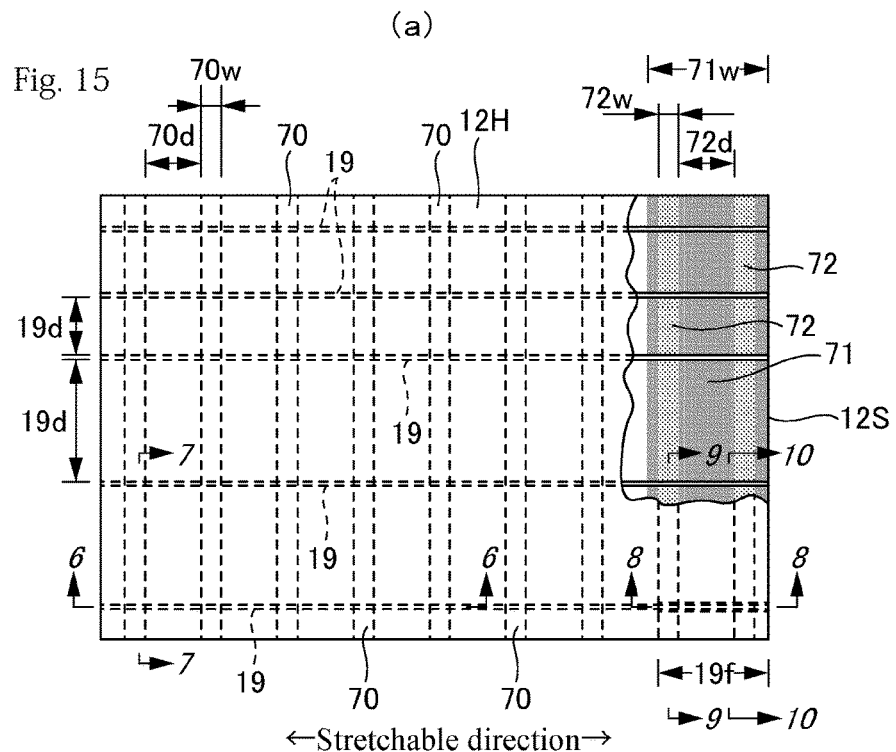
←Stretchable direction→
(b)
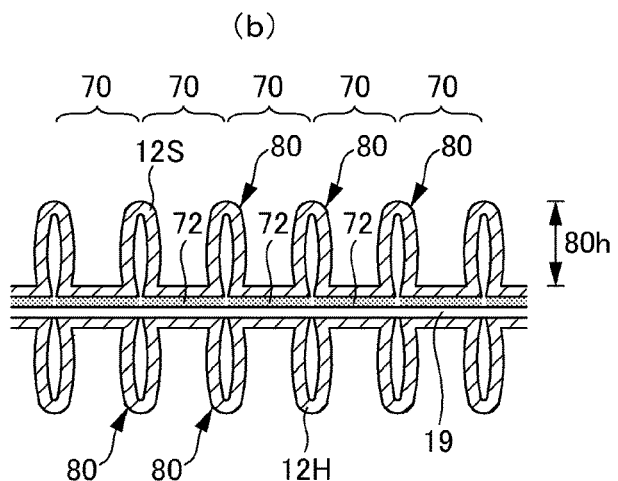
(c)
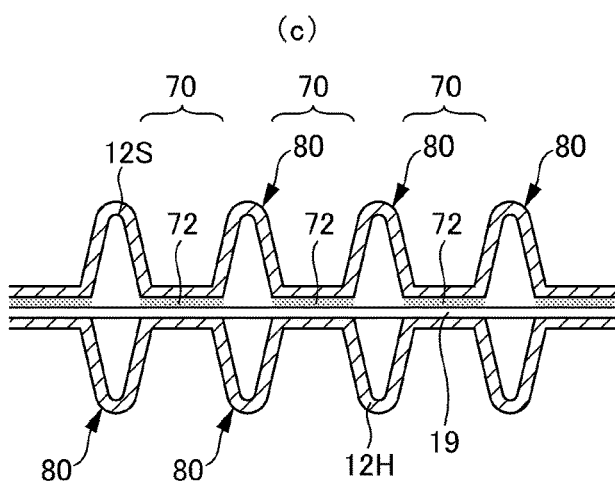

Fig. 16
(d)
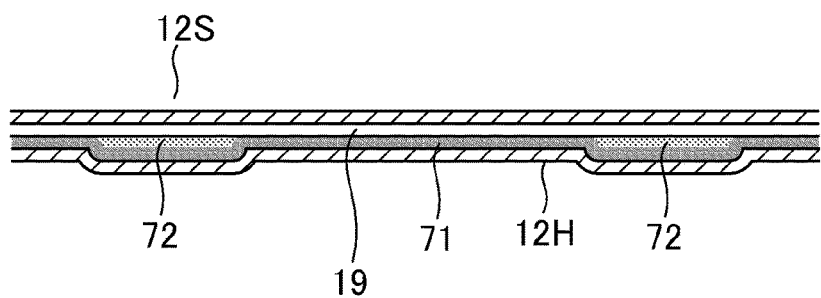
(e) (f) (g)
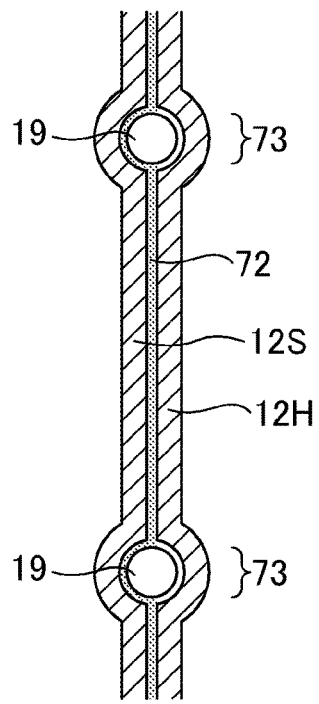 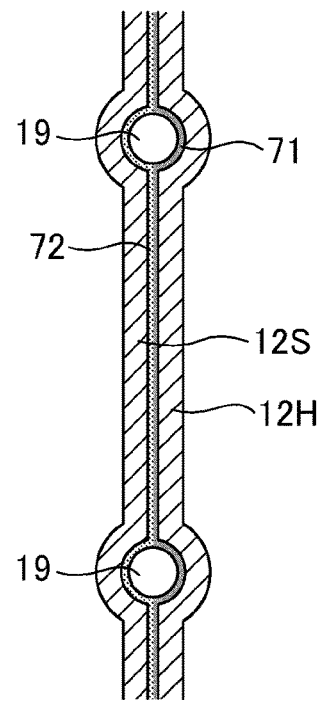 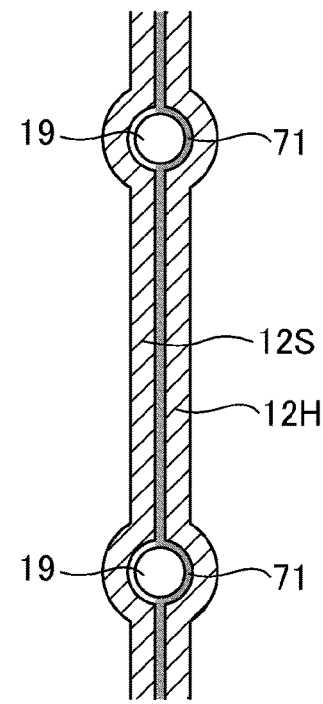

←Stretchable direction→

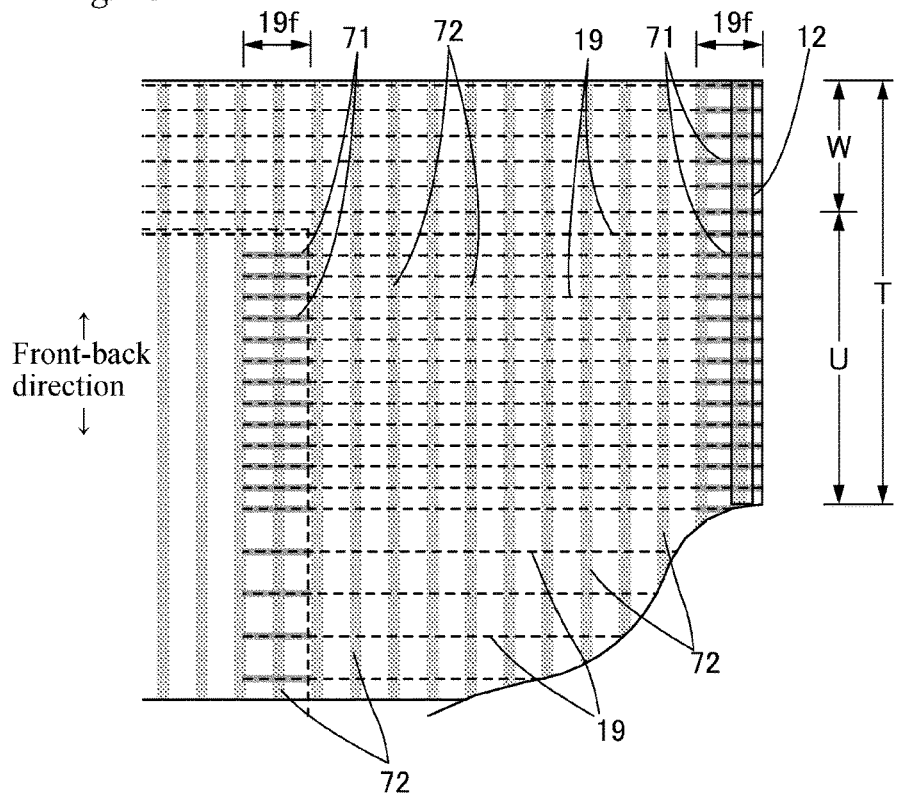
Fig. 18
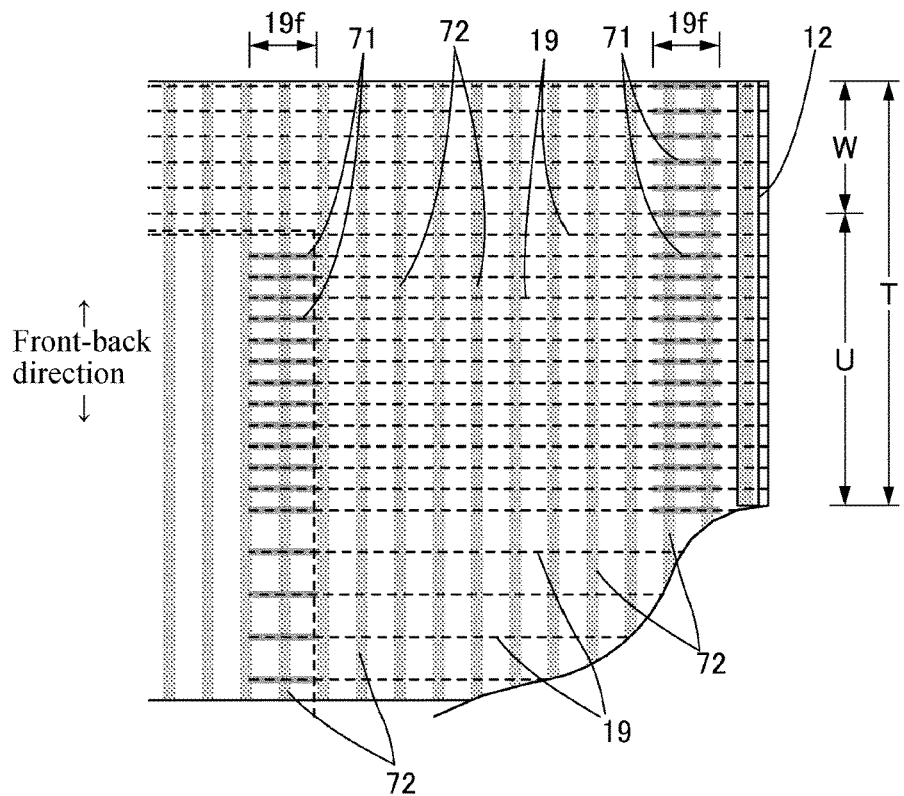

Fig. 20
(a)
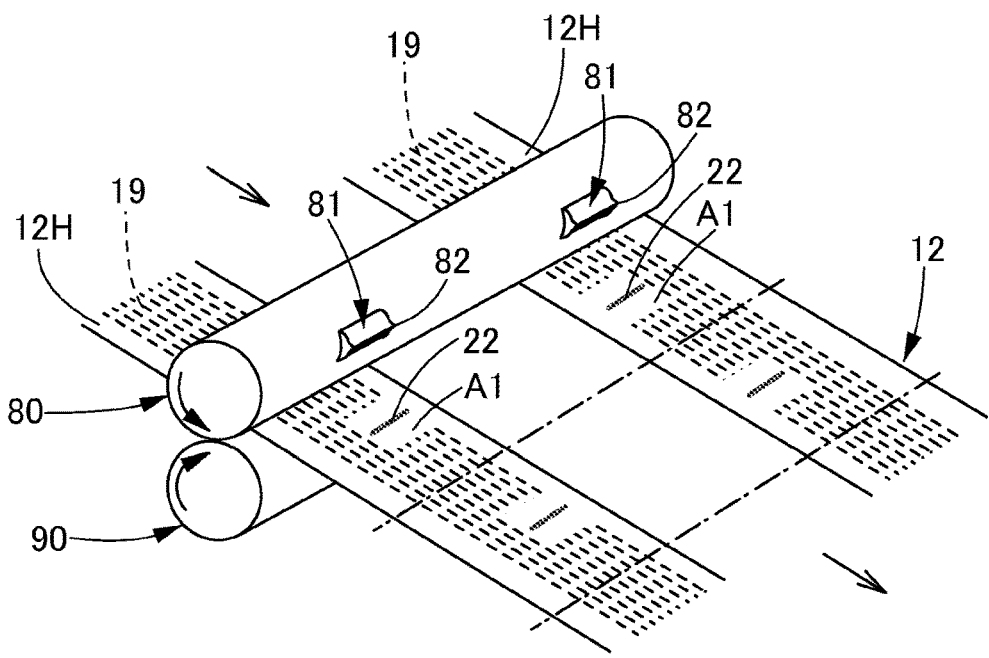
(b)
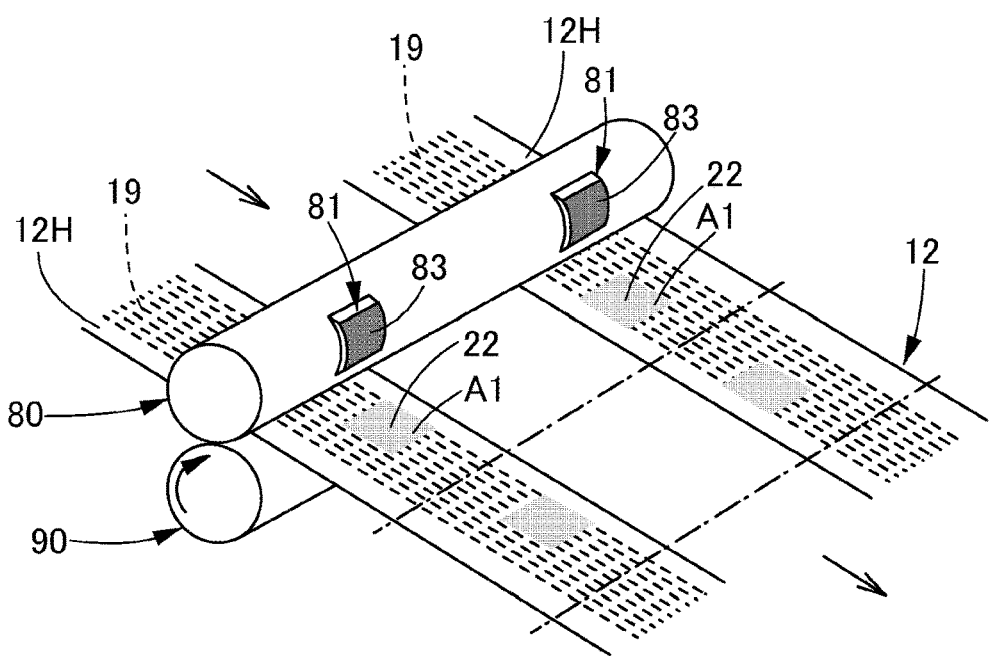

Fig. 21
(a) 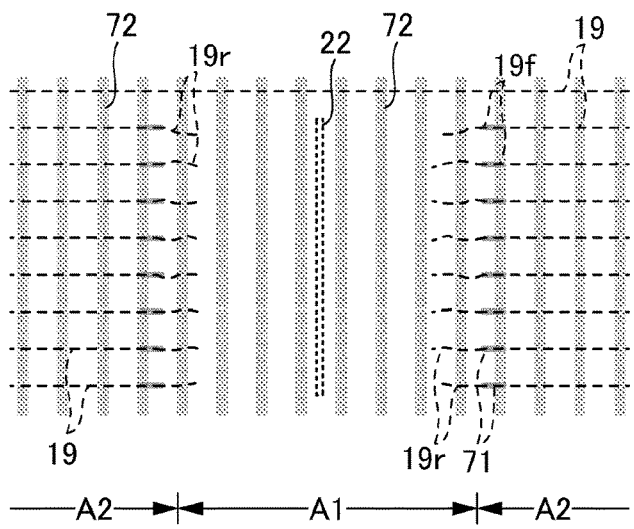
(b) 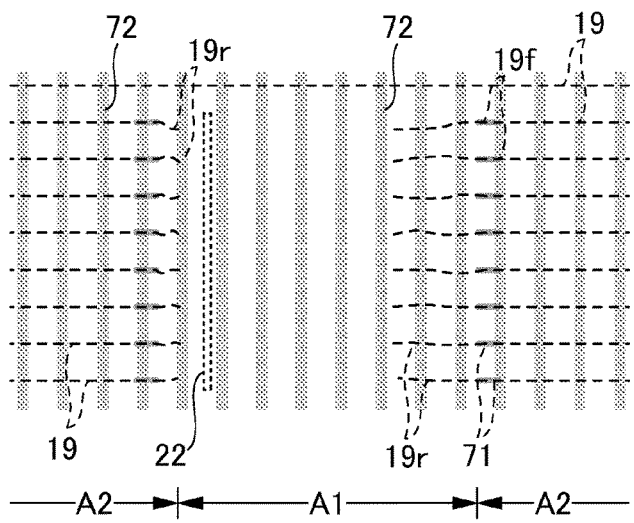
(c) 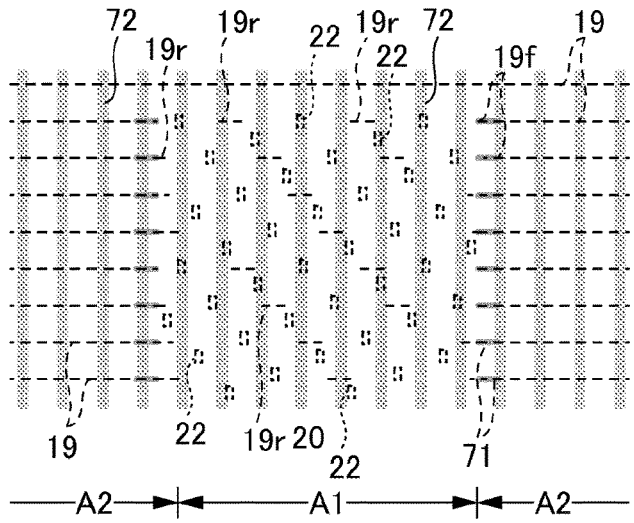

STRETCHABLE STRUCTURE OF ABSORBENT ARTICLE AND MANUFACTURING METHOD OF THE SAME

CROSS-REFERENCE TO RELATED APPLICATIONS

This application is the U.S. national stage application of International Application PCT/JP2017/006708, filed Feb. 23, 2017, which international application was published on Oct. 5, 2017, as International Publication WO 2017/169338 in the Japanese language. The International Application claims priority of Japanese Patent Application No. 2016-069153, filed Mar. 30, 2016. The international application and Japanese application are both incorporated herein by reference, in entirety.

TECHNICAL FIELD

The present invention relates to a stretchable structure of an absorbent article and a method of manufacturing the stretchable structure of an absorbent article.

BACKGROUND ART

In general, a stretchable structure is provided in an absorbent article to improve fitting property of each part. For example, in a disposable diaper of an underpants-type or a tape-type, it has been widely practiced to provide the stretchable structure in a lower torso portion along the circumferential direction thereof or to provide the stretchable structure in leg portions along the circumferential direction thereof. Further, it is widely practiced to provide the stretchable structure in the front-back direction called a "three-dimensional gather" and a "plane gather" over an absorbent article including a sanitary napkin as well as a disposable diaper of an underpants-type and a tape-type.

As a stretchable structure of such an absorbent article, the applicant of the present invention has proposed the stretchable structure described in Patent Literatures 1 and 2. That is, the stretchable structure of the absorbent article includes a first sheet layer made of a nonwoven fabric, a second sheet layer made of a nonwoven fabric and opposed to one side of the first sheet layer, and a plurality of elongated elastically stretchable members provided at intervals from each other along the stretchable direction between the first sheet layer and the second sheet layer. The first sheet layer and the second sheet layer are bonded via a hot melt adhesive disposed in a striped pattern intermittent in the longitudinal direction of the elastically stretchable members and continuously elongated in a direction intersecting with the elastically stretchable members (hereinafter also referred to as a "bonding mode being continuous in the direction intersecting the elastically stretchable members"). In this stretchable structure, at the time of a natural length state and in a wearing state in which the structure is contracted to some extent, with contraction of the elastically stretchable members, portions positioned between sheet bonded portions of the first sheet layer and the second sheet layer contract and are raised in the opposite directions from each other to form pleats. In addition, since the pleats extend straightly along the sheet bonded portions, air permeability and appearance are excellent.

However, it is extremely difficult to stably apply a hot melt adhesive 72 in a striped pattern which is intermittent in the longitudinal direction of elastically stretchable members 19 and elongated continuously in the direction intersecting with the elastically stretchable members 19 as illustrated in FIG. 22, and since strings 75 are stretching out from application portions of the hot melt adhesive 72 to a downstream side in the flow direction of the manufacturing line, fine point-like scattering portions 76 are generated, and the like, a first sheet layer 12S and a second sheet layer 12H are therefore adhered at portions to be pleats (portions between adjacent applications of the hot melt adhesive 72) although these portions are supposed to be non-adhesive portions. This causes a problem that the pleats are collapsed or irregularly deformed there, and the appearance deteriorates.

CITATION LIST

Patent Literature

Patent Literature 1: JP 2014-207973 A
Patent Literature 2: JP 2014-198178 A

SUMMARY OF THE INVENTION

Technical Problem

Therefore, the main object of the present invention is to prevent deterioration of appearance of pleats due to unintended adhesion.

Solution to Problem

The inventors of the present invention have confirmed during manufacturing experiments on the stretchable structure using various materials for the first sheet layer and the second sheet layer that if it is difficult to adhere either one of the opposing faces with a hot melt adhesive, it results in preventing unintended adhesion under insufficient adhesion conditions such as stringiness and/or scattering of a hot melt adhesive. The present invention described below is based on such findings.

<Invention According to Claim 1>

A stretchable structure of an absorbent article, comprising:

a first sheet layer made of a nonwoven fabric; a second sheet layer made of a nonwoven fabric and opposed to one side surface of the first sheet layer; and a plurality of elongated elastically stretchable members provided along the stretchable direction at intervals from each other between the first sheet layer and the second sheet layer, wherein the first sheet layer and the second sheet layer have sheet bonded portions bonded via a hot melt adhesive disposed in a striped pattern that is intermittent in the longitudinal direction of the elastically stretchable members and continuously elongated in the direction intersecting with the elastically stretchable members, and either one of the first sheet layer and the second sheet layer is made of a low-adhesion nonwoven fabric having lower peel strength with respect to a hot melt adhesive than the other sheet layer.

(Function and Effect)

The feature of the present invention lies in the fact that the low-adhesion nonwoven fabric having poor adhesiveness with respect to the hot melt adhesive is intentionally used as one adhesion surface. As a result, even if stringiness and/or scattering of the hot melt adhesive occurs, under such insufficient adhesion conditions, the first sheet layer and the second sheet layer are not bonded or are peeled off immediately even if being bonded to some extent. Therefore, deterioration of appearance of the pleats, which would be caused by the unintended adhesion, is effectively prevented. In addition, both of the adhesive surfaces made of the low-adhesion nonwoven fabrics would cause a possibility that the sheet bonded portions to be bonded would not be bonded sufficiently. However, in the present invention, the sheet bonded portions are reliably bonded because just one adhesive surface is made of low-adhesion nonwoven fabric, and consequently, the pleats excellent in appearance are formed.

In the present invention, "hot melt adhesive is continuous" means, at intersection portions of the sheet bonded portions and the elastically stretchable members, that the hot melt adhesive is continuously applied to both the first sheet layer-side and the second sheet layer-side of the elastically stretchable members in the direction intersecting with the stretchable direction, as well as that the hot melt adhesive is continuous in one side due to the elastically stretchable members interposed but the hot melt adhesive is discontinuous in the direction intersecting with the stretchable direction on the other side.

<Invention According to Claim 2>

The stretchable structure of an absorbent article according to claim 1, wherein at intersection portions of the sheet bonded portions and the elastically stretchable members, the hot melt adhesive is continuous in the direction intersecting with the elastically stretchable members on the nonwoven fabric side being not the low-adhesion nonwoven fabric side of the elastically stretchable members, and the hot melt adhesive is discontinuous in the direction intersecting with the elastically stretchable members on the low-adhesion nonwoven fabric side of the elastically stretchable members.

(Function and Effect)

Thus, when the hot melt adhesive is continuous on the nonwoven fabric since being not the low-adhesion nonwoven fabric side of the elastically stretchable members, the adhesiveness at the sheet bonded portions increases. Furthermore, since the hot melt adhesive is discontinuous on the low-adhesion nonwoven fabric side of the elastically stretchable members, the flexibility of the low-adhesion nonwoven fabric is not easily impaired.

<Invention According to Claim 3>

The stretchable structure of an absorbent article according to claim 1 or 2, wherein the hot melt adhesive has a melt viscosity of 10,000 to 40,000 mPa·s at a temperature of 140° C., a melt viscosity of 5,000 to 10,000 mPa·s at a temperature of 160° C., and a loop tack adhesive strength of 10 to 500 g/25 mm (Function and Effect)

As a hot melt adhesive for forming sheet bonded portions, the hot melt adhesive having a low melt viscosity and a high loop tack adhesive strength is preferable in that the adhesiveness to a nonwoven fabric is excellent, but with such hot melt adhesive, stringiness and/or scattering are likely to occur in manufacturing. However, in the present invention, unintended adhesion is unlikely to occur even if stringiness and/or scattering of the hot melt adhesive occurs. Therefore, it is also possible to use such a hot melt adhesive having high adhesiveness to a nonwoven fabric.

<Invention According to Claim 4>

The stretchable structure of an absorbent article according to any one of claims 1 to 3, wherein the width of each sheet bonded portion in the stretchable direction is 0.5 to 4 mm, and the interval between adjacent sheet bonded portions is 4 to 8 mm (Function and Effect)

When the sheet bonded portions by the hot melt adhesive are disposed in these dimensions (the bonding mode being continuous in the direction intersecting the elastically stretchable members), formed pleats are extended straightly and also have sufficient height but rarely fall.

To be more specific, the width in the stretchable direction of each sheet bonded portion affects the interval between adjacent pleats. If the pleat to be formed is thin, when the width is larger than 4 mm, the space between adjacent pleats becomes too wide, and individual pleats have independent appearance. In addition, when the pleats deform for example, collapse and spread and fall due to a compressive force in the thickness direction, the effect of mutual support of the adjacent pleats weakens. As a result, resistance with respect to the deformation and restoration after the deformation also weaken, and fullness becomes insufficient.

In addition, by merely setting the width of the sheet bonded portion in the stretchable direction to 0.5 to 4 mm, when the interval between adjacent sheet bonded portions is less than 4 mm or more than 8 mm, the following situation will be caused. That is, the interval between the adjacent sheet bonded portions affects the height and width of pleats, and if the interval between adjacent sheet bonded portions is about 2 mm, the pleats have poor continuity in the orthogonal direction as with the case of continuously bonding in the stretchable direction (it has no meaning to provide sheet bonded portions intermittently in the stretchable direction). If the interval is 3 mm, the pleats straightly extend in the direction orthogonal to the stretchable direction, but the effect of mutual support of the adjacent pleats cannot be expected, which results in insufficient fullness. In addition, when the interval between the sheet bonded portions exceeds 8 mm, the pleats are collapsed irregularly due to the compression during wrapping, and the product appearance deteriorates. On the other hand, when the width of the sheet bonded portion in the stretchable direction is 0.5 to 4 mm, and the interval between the adjacent sheet bonded portions is 4 to 8 mm, sufficient fullness can be finally obtained, and against the compression during wrapping, the pleats are unlikely to be collapsed irregularly.

Further, in the case of having the sheet bonded portions with such a pattern, stringiness and/or scattering of the hot melt adhesive tends to occur due to a narrow application width of the hot melt adhesive. Therefore, the present invention is particularly suitable when the sheet bonded portions are formed with such dimensions.

<Invention According to Claim 5>

The stretchable structure of an absorbent article according to any one of claims 1 to 4, wherein the low-adhesion nonwoven fabric has a higher area rate of concaves and a larger number of concaves per unit area than the nonwoven fabric being not the low-adhesion nonwoven fabric.

(Function and Effect)

For example, since heat embossing is used for fiber bonding in a spunbond nonwoven fabric, a large number of concaves are formed in a predetermined pattern on the surface, and for the other nonwoven fabric, heat embossing is separately performed to form a large number of concaves in a predetermined pattern on the surface. The degree of the area rate of the concaves and the number of the concaves per unit area (including whether or not the concaves are formed) affect the adhesiveness of the hot melt adhesive. That is, the higher the area rate of the concaves is and the larger the number of the concaves per unit area is, the smaller the adhesiveness is. Therefore, the nonwoven fabrics having such differences in terms of the concaves can be suitably used as the low-adhesion nonwoven fabric and the nonwoven fabric being not the low-adhesion nonwoven fabric. In this method, there is also an advantage that the nonwoven fabrics having the same properties except ones regarding the concaves can be used in the first sheet layer and the second sheet layer.

<Invention According to Claim 6>

The stretchable structure of an absorbent article according to any one of claims 1 to 5, wherein the low-adhesion nonwoven fabric has a higher content of a water repellent agent than the nonwoven fabric being not the low-adhesion nonwoven fabric, or the water repellent agent is externally added to the low-adhesion nonwoven fabric and the water repellent agent is internally added to the nonwoven fabric being not the low-adhesion nonwoven fabric.

(Function and Effect)

It has been widely practiced to add a water repellent agent to a nonwoven fabric to form a water repellent nonwoven fabric, and the difference in the content of the water repellent agent (including whether or not the water repellent agent is added) or the difference between the internal and external additions affects the adhesiveness of a hot melt adhesive. That is, the higher the content is, the lower the adhesiveness is, and the adhesiveness by the external addition is lower than the adhesiveness by the internal addition. Therefore, the nonwoven fabrics having such differences in terms of the water repellent agent can be suitably used as the low-adhesion nonwoven fabric and the nonwoven fabric being not the low-adhesion nonwoven fabric. In this method, there is also an advantage that the nonwoven fabrics having the same properties except ones regarding the water repellent agent can be used in the first sheet layer and the second sheet layer.

<Invention According to Claim 7>

The stretchable structure of an absorbent article according to any one of claims 1 to 6, wherein the low-adhesion nonwoven fabric has a higher content of a softening agent than the nonwoven fabric being not the low-adhesion nonwoven fabric, or the softening agent is externally added to the low-adhesion nonwoven fabric and the softening agent is internally added to the nonwoven fabric being not the low-adhesion nonwoven fabric.

(Function and Effect)

It has been widely practiced to add a softening agent to a nonwoven fabric, and the difference in the content of the softening agent (including whether or not the softening agent is added) or the difference between the internal and external additions affects the adhesiveness of a hot melt adhesive. That is, the higher the content is, the lower the adhesiveness is, and the adhesiveness by the external addition is lower than the adhesiveness by the internal addition. Therefore, nonwoven fabrics having such differences in terms of the softening agent can be suitably used as the low-adhesion nonwoven fabric and the nonwoven fabric being not the low-adhesion nonwoven fabric. In this method, there is also an advantage that the nonwoven fabrics having the same properties except ones regarding the softening agent can be used in the first sheet layer and the second sheet layer.

<Invention According to Claim 8>

The stretchable structure of an absorbent article according to any one of claims 1 to 7, wherein the absorbent article is an underpants-type disposable diaper, in which an outer member disposed in a front body and a back body and an inner member attached to the outer member and including an absorber are provided, both side edges of the outer member of the frond body and both side edges of the outer member of the back body are bonded to each other, a range corresponding in the front-back direction to the bonded side edges is an annular lower torso portion, and a waist opening and a pair of right and left leg openings are formed and wherein the stretchable structure is provided in a region including at least both sides in the width direction of the inner member in the outer member such that the elastically stretchable members extend along the width direction, the low-adhesion nonwoven fabric is on the outside, and the nonwoven fabric being not the low-adhesion nonwoven fabric is on the inside.

(Function and Effect)

As described above, the stretchable structure according to the present invention is suitable for the region including at least both sides in the width direction of the inner member in the outer member of the underpants-type disposable diaper. In particular, since the outer surface of the outer member is made of the low-adhesion nonwoven fabric, the appearance of pleats on the outer surface of the product is hardly deteriorated.

<Invention According to Claim 9>

A method of manufacturing a stretchable structure of an absorbent article, comprising:

using a first sheet layer and a second sheet layer either one of which is made of a low-adhesion nonwoven fabric having lower peel strength with respect to a hot melt adhesive than the other sheet layer;

sandwiching a plurality of elongated elastically stretchable members provided along the stretchable direction at intervals from each other between the first sheet layer and the second sheet layer; and forming sheet bonded portions by bonding the first sheet layer and the second sheet layer via the hot melt adhesive disposed in a striped pattern that is intermittent in a longitudinal direction of the elastically stretchable members and continuously elongated in a direction intersecting with the elastically stretchable members.

(Function and Effect)

The same functions and effects as those obtained in the invention according to claim 1 are obtained.

<Invention According to Claim 10>

The method of manufacturing the stretchable structure of an absorbent article according to claim 9, wherein in the forming of the sheet bonded portions, the hot melt adhesive is applied to the nonwoven fabric being not the low-adhesion nonwoven fabric in the striped pattern that is intermittent in the longitudinal direction of the elastically stretchable members and continuously elongated in the direction intersecting with the elastically stretchable members, and the hot melt adhesive is not applied to the low-adhesion nonwoven fabric.

(Function and Effect)

The same functions and effects as those obtained in the invention according to claim 2 are obtained.

<Invention According to Claim 11>

The method of manufacturing the stretchable structure of an absorbent article according to claim 9 or 10, wherein the hot melt adhesive has a melt viscosity of 10,000 to 40,000 mPa·s at a temperature of 140° C., a melt viscosity of 5,000 to 10,000 mPa·s at a temperature of 160° C., and a loop tack adhesive strength of 10 to 500 g/25 mm (Function and Effect)

The same functions and effects as those obtained in the invention according to claim 3 are obtained.

<Invention According to Claim 12>

The method of manufacturing the stretchable structure of an absorbent article according to any one of claims 9 to 11, comprising:

a step of applying the hot melt adhesive in which at least one of the first sheet layer and the second sheet layer is brought into contact with an engraved roll such that a circumferential direction of the engraved roll is a stretchable direction, and the hot melt adhesive, which is held in the striped pattern that is intermittent in the circumferential direction and continuous in the axial direction on the outer peripheral surface of the engraved roll, is transferred on at least one of the first sheet layer and the second sheet layer; and a step of performing pressure bonding in which the elastically stretchable members are sandwiched between the first sheet layer and the second sheet layer on at least one of which the hot melt adhesive is transferred, wherein in the step of applying the hot melt adhesive, on the outer peripheral surface of the engraved roll, the application width in the circumferential direction of the hot melt adhesive is set to 0.5 to 4 mm, and the interval between the adjacent applications in the circumferential direction of the hot melt adhesive is set to 4 to 8 mm.

(Function and Effect)

The same functions and effects as those obtained in the invention according to claim 4 are obtained. Further, in such a pattern application by the transfer with the roll, although the application width of the hot melt adhesive can be narrowed, stringiness and/or scattering are likely to occur. Therefore, this claim is particularly suitable for applying the present invention.

<Invention According to Claim 13>

The method of manufacturing the stretchable structure of an absorbent article according to any one of claims 9 to 12, wherein the low-adhesion nonwoven fabric has a higher area rate of concaves and a larger number of concaves per unit area than the nonwoven fabric being not the low-adhesion nonwoven fabric.

(Function and Effect)

The same functions and effects as those obtained in the invention according to claim 5 are obtained.

<Invention According to Claim 14>

The method of manufacturing the stretchable structure of an absorbent article according to any one of claims 9 to 13, wherein the low-adhesion nonwoven fabric has a higher content of a water repellent agent than the nonwoven fabric being not the low-adhesion nonwoven fabric, or the water repellent agent is externally added to the low-adhesion nonwoven fabric and the water repellent agent is internally added to the nonwoven fabric being not the low-adhesion nonwoven fabric.

(Function and Effect)

The same functions and effects as those obtained in the invention according to claim 6 are obtained.

<Invention According to Claim 15>

The method of manufacturing the stretchable structure of an absorbent article according to any one of claims 9 to 14, wherein the low-adhesion nonwoven fabric has a higher content of a softening agent than the nonwoven fabric being not the low-adhesion nonwoven fabric, or the softening agent is externally added to the low-adhesion nonwoven fabric, and the softening agent is internally added to the nonwoven fabric being not the low-adhesion nonwoven fabric.

(Function and Effect)

The same functions and effects as those obtained in the invention according to claim 7 are obtained.

Advantage Effects of Invention

As described above, according to the present invention, it is possible to prevent deterioration of appearance of pleats due to unintended adhesion, and the like.

BRIEF DESCRIPTION OF DRAWINGS

FIG. 11(a) is a plan view of a stretchable structure in a spread state. FIG. 11(b) is a cross-sectional view taken along line 6-6 in a natural length state. FIG. 11(c) is a cross-sectional view taken along line 6-6 in a state stretched to some extent.

FIG. 12(d) is a cross-sectional view taken along line 8-8 in FIG. 11. FIG. 12(e) is a cross-sectional view taken along line 7-7 in FIG. 11. FIG. 12(f) is a cross-sectional view taken along line 9-9 in FIG. 11. FIG. 12(g) is a cross-sectional view taken along line 10-10 in FIG. 11.

FIG. 13(a) is a plan view of a stretchable structure in a spread state. FIG. 13(b) is a cross-sectional view taken along line 6-6 in a natural length state. FIG. 13(c) is a cross-sectional view taken along line 6-6 in a state stretched to some extent.

FIG. 14(d) is a cross-sectional view taken along line 8-8 in FIG. 13. FIG. 14(e) is a cross-sectional view taken along line 7-7 in FIG. 13. FIG. 14(f) is a cross-sectional view taken along line 9-9 in FIG. 13. FIG. 14(g) is a cross-sectional view taken along line 10-10 in FIG. 13.

FIG. 15(a) is a plan view of a stretchable structure in a spread state. FIG. 15(b) is a cross-sectional view taken along line 6-6 in a natural length state. FIG. 15(c) is a cross-sectional view taken along line 6-6 in a state stretched to some extent.

FIG. 16(d) is a cross-sectional view taken along line 8-8 in FIG. 15. FIG. 16(e) is a cross-sectional view taken along line 7-7 in FIG. 15. FIG. 16(f) is a cross-sectional view taken along line 9-9 in FIG. 15. FIG. 16(g) is a cross-sectional view taken along line 10-10 in FIG. 15.

FIG. 18 is a plan view illustrating a main part of an outer member in a spread state.

FIG. 20 is a perspective view of a cutting device.

FIG. 21 is an enlarged plan view of a main part indicating various embodiments for cutting in a non-stretchable region.

DESCRIPTION OF EMBODIMENTS

Hereinafter, embodiments of the present invention will be described in detail with reference to the accompanying drawings.

FIGS. 1 to 6 illustrate an example of an underpants-type disposable diaper 100. This underpants-type disposable diaper 100 is composed of an outer member 12 disposed in an outer surface (back surface side) of a product and an inner member 200 attached to the outer member 12. The reference sign 201 denotes a region where the inner member 200 and the outer member 12 are fixed. The reference sign Y denotes the maximum length of the diaper. The reference sign X denotes the maximum width of the diaper.

The inner member 200 is a portion to absorb and hold excrement such as urine, and the outer member 12 is a portion to attach the inner member 200 to the body of a wearer. In addition, the dotted portions in the cross-sectional view indicate bonded portions to bond respective component members, and the bonded portions are formed by, for example solid, bead, curtain, summit, or spiral application of a hot melt adhesive or the like.

(Inner Member)

Figure 3:
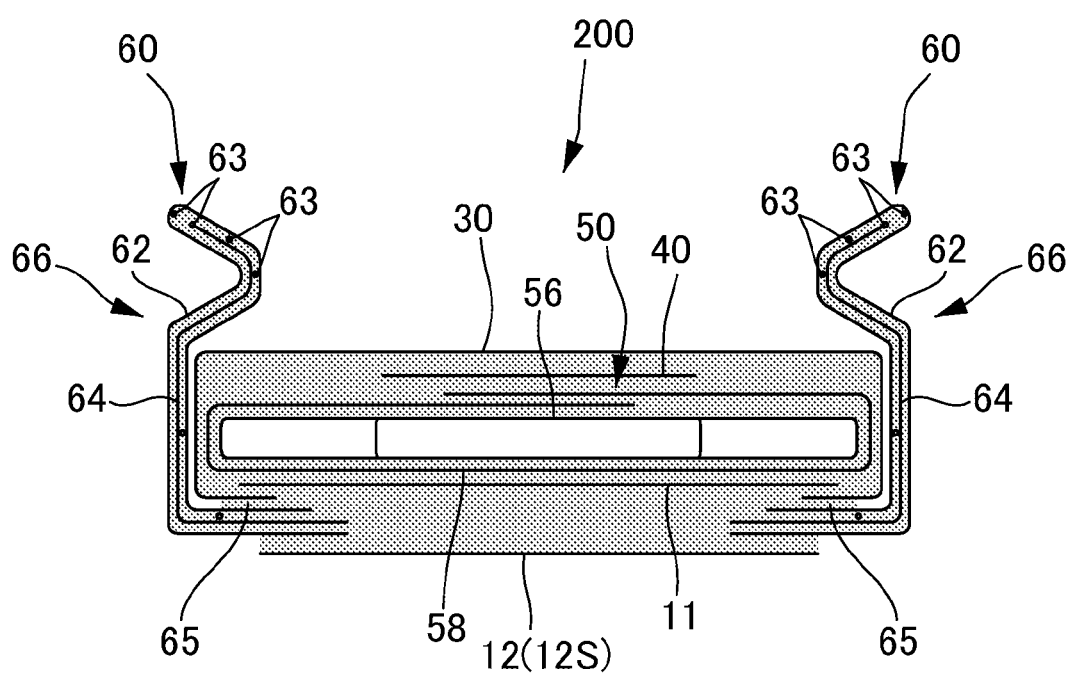
FIG. 3 is a cross-sectional view taken along line 3-3 in FIG. 1.
Figure 4:
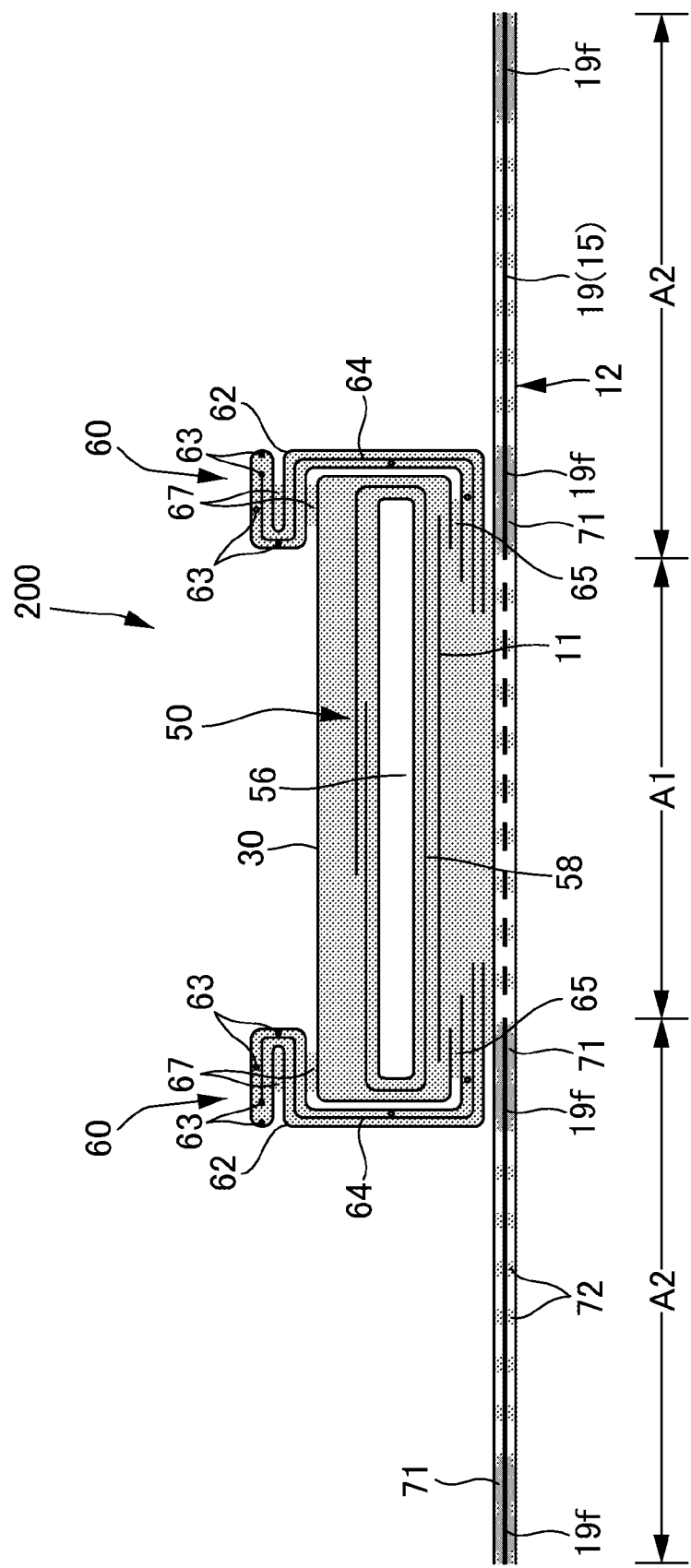
FIG. 4 is a cross-sectional view taken along line 4-4 in FIG. 1.
Figure 5:
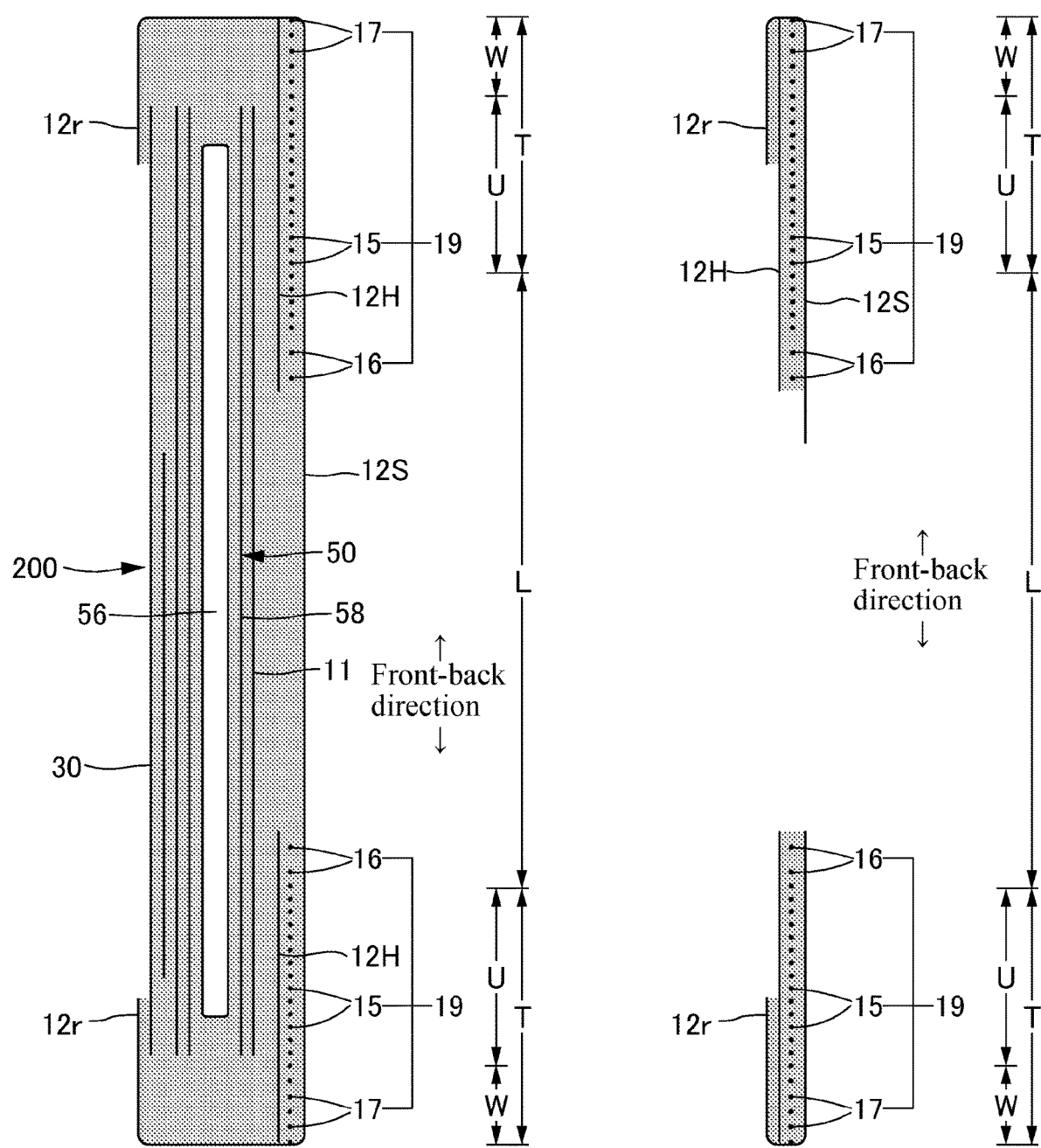
FIG. 5(a) is a cross-sectional view taken along line 5-5 in FIG. 1.
FIG. 5(b) is a cross-sectional view taken along line 2-2 in FIG. 1.

The inner member 200 can have an arbitrary shape, but in the illustrated embodiment, it is rectangular. As illustrated in FIGS. 3 to 5, the inner member 200 is provided with a top sheet 30 which is in contact with the skin, a liquid impervious sheet 11, and an absorbent element 50 interposed therebetween, and is a main unit section that plays a role of an absorbent function. The reference sign 40 denotes an intermediate sheet (second sheet) provided between the top sheet 30 and the absorbent element 50 in order to promptly transfer liquid having permeated through the top sheet 30 to the absorbent element 50. The reference sign 60 denotes three-dimensional gathers 60 provided on both sides of the inner member 200 and standing on the skin side of a wearer in order to prevent excrement from leaking to both sides of the inner member 200.

(Top Sheet)

The top sheet 30 has a property of permeating liquid, and examples of the top sheet 30 include a perforated or non-porous nonwoven fabric and a porous plastic sheet. Among them, a raw fiber of the nonwoven fabric is not particularly limited. Examples of the raw fiber include synthetic fibers such as olefin such as polyethylene and polypropylene, polyester, and polyamide, regenerated fibers such as rayon and cupra, natural fibers such as cotton, and mixed fibers and composite fibers in which two or more of these are used.

Further, the nonwoven fabric may be manufactured by any processing. Examples of the processing method include known methods such as a spunlace method, a spunbond method, a thermalbond method, a meltblown method, a needlepunch method, an air through method, and a point-bond method. For example, if flexibility and drapeability are required, the spunbond method and the spunlace method are preferable processing methods, and if bulkiness and softness are required, the air through method, the point bond method, and the thermalbond method are preferable processing methods.

Further, the top sheet 30 may be made of one sheet or a laminated sheet obtained by bonding two or more sheets. Similarly, the top sheet 30 may be composed of one sheet or two or more sheets with respect to the plane direction.

In the case of providing the three-dimensional gathers 60, it is preferable that both side edges of the top sheet 30 are extended between the liquid impervious sheet 11 and the three-dimensional gathers 60 and to the back face of the absorbent element 50 and bonded to the liquid impervious sheet 11 and the three-dimensional gathers 60 with a hot melt adhesive or the like to prevent liquid permeation.

(Intermediate Sheet)

An intermediate sheet (also called a "second sheet") 40 can be provided between the top sheet 30 and the absorbent element 50. This intermediate sheet 40 not only improves the absorption performance by an absorber 56 by immediately moving liquid to the absorber 56 side, but also prevents the absorbent liquid from returning from the absorber 56 and makes the surface of the top sheet 30 dry. The intermediate sheet 40 can also be omitted.

Examples of the intermediate sheet 40 include the same material as the top sheet 30, a spunlace, a spunbond, SMS, a pulp nonwoven fabric, a mixed sheet of pulp and rayon, a pointbond, or a crepe paper. In particular, an air-through nonwoven fabric is preferable because it is bulky. It is preferable to use a composite fiber having a core-sheath structure for the air-through nonwoven fabric. In this case, resin used for the core may be polypropylene (PP), but polyester (PET) having high rigidity is preferable. The basis weight is preferably 20 to 80 g/m$^2$, more preferably 25 to 60 g/m$^2$. The fineness of the raw fiber of the nonwoven fabric is preferably 2.2 to 10 dtex. To increase the bulkiness of the nonwoven fabric, it is also preferable to use eccentric fibers, hollow fibers, eccentric and hollow fibers, whose core is not in the center, as mixed fibers of all or a part of the raw material fibers.

The intermediate sheet 40 in the illustrated embodiment is disposed at the center shorter than the width of the absorber 56, but may be provided over the maximum width. The length of the intermediate sheet 40 in the longitudinal direction may be the same as the length of the absorber 56 or may be within a short length range centered on the liquid receiving area.

(Liquid Impervious Sheet)

The material of the liquid impervious sheet 11 is not particularly limited, but examples of the material include a plastic film made of an olefin resin such as polyethylene and polypropylene, a laminated nonwoven fabric having a plastic film on the surface of a nonwoven fabric, and a laminated sheet obtained by bonding nonwoven fabrics or the like on a plastic film. In the liquid impervious sheet 11, in recent years, it is preferable to use a material having liquid impermeability and moisture permeability that has been favorably used from the viewpoint of prevention of stuffiness. As the moisture-permeable plastic film, a microporous plastic film is widely used. The microporous plastic film is obtained by stretching a sheet in a monoaxial or biaxial direction after forming the sheet by kneading an inorganic filler in an olefin-based resin such as polyethylene or polypropylene. In addition to this, a nonwoven fabric sheet of microdenier fiber and a liquid impervious sheet without a plastic film having reinforced leakage-resistance achieved by applying heat and pressure to reduce the gaps between the fibers or by application with super absorbent resin, a hydrophobic resin, or a water repellent agent can also be used as the liquid impervious sheet 11.

To enhance leakage resistance, the liquid impervious sheet 11 can also be disposed around the both side faces of the absorbent element 50 to extend to the both sides of the side surface of the top sheet 30 of the absorbent element 50.

Further, on the inside of the liquid impervious sheet 11, in particular, on the side surface of the absorber 56, an excretion indicator that changes its color due to absorption of a liquid component can be provided.

(Three-Dimensional Gather)

The three-dimensional gathers 60 are strip-shaped members extending along the both side edges of the inner member 200 in the front-back direction. The three-dimensional gather 60 is provided to block fluid excretion (urine, loose stools, etc.) moving on the top sheet 30 in the lateral direction and to prevent lateral leakage. The three-dimensional gather 60 according to the present embodiment is provided so as to stand upright from the side portion of the inner member 200, the root side portion stands obliquely toward the center side in the width direction, and the portion closer to the tip side than the intermediate portion stands obliquely toward the outside in the width direction. Although this embodiment is a surface contact type three-dimensional gather, a line contact type three-dimensional gather (not illustrated) which is not folded back outward in the width direction can also be used.

To be more specific, the three-dimensional gather 60 includes a belt shaped gather sheet 62 having a length equal to the length in the front-back direction of the inner member 200 and folded back in two in the width direction, and a plurality of elongated elastically stretchable members 63 fixed along the longitudinal direction with intervals in the width direction in a stretched state between sheets in the folded portion and the neighboring portions. An end portion on the opposite side to the folded portion in the width direction in the three-dimensional gather 60 is an attachment portion 65 fixed to the rear surface of the side edge portion of the inner member 200. A portion other than the attachment portion 65 is a protruding portion 66 (a portion on the folded portion side) protruding from the attachment portion 65. The both ends of the protruding portion 66 in the front-back direction extend from the attachment portion 65 to the surface of the side portion of the top sheet 30 through the side of the inner member 200, and the both ends are fallen portions fixed by a fixing means such as the hot melt adhesive 67 with respect to the surface of the side portion of the top sheet 30. The intermediate portion in the front-back direction of the protruding portion 66 is a non-fixed free portion, and the elongated elastically stretchable members 63 along the front-back direction are fixed in a stretched state at least over the entire front-back direction of the free portion.

As the gather sheet 62, a nonwoven fabric which is flexible and excellent in uniformity and concealing property such as a spunbond nonwoven fabric (SS, SSS, etc.), SMS nonwoven fabric (SMS, SSMMS etc.), meltblown nonwoven fabric, and on which a water repellent process is performed by silicone as necessary, can be preferably used, and the fiber basis weight is preferably set to about 10 to 30 g/m$^2$. As the elongated elastically stretchable member 63, a rubber thread and the like can be used. When a spandex rubber thread is used, the fineness is preferably 470 to 1240 dtex, more preferably 620 to 940 dtex. The stretch rate at the time of fixing is preferably from 150 to 350%, more preferably from 200 to 300%. The term "stretch rate" means a value when the natural length is taken as 100%. As illustrated in the drawing, a waterproof film 64 may be interposed between gather sheets folded in two.

The number of the elongated elastically stretchable members 63 provided in the free portion of the three-dimensional gather 60 is preferably two to six, more preferably three to five. An appropriate arrangement interval 60$d$ is 3 to 10 mm With such a configuration, a range in which the elongated elastically stretchable members 63 are disposed easily comes into surface contact with the skin. The elongated elastically stretchable members 63 may be disposed not only on the tip side but also on the root side.

The target to which the attachment portion 65 of the three-dimensional gather 60 is fixed can be an appropriate member such as the top sheet 30, the liquid impervious sheet 11, and the absorbent element 50 in the inner member 200.

In the three-dimensional gathers 60 formed as described above, a contraction force of the elongated elastically stretchable members 63 acts so as to bring both ends in the front-back direction close to each other, but both ends in the front-back direction of the protruding portions 66 are fixed in a fallen state, and spaces between the both ends are non-fixed free portions. Therefore, only the free portions stand so as to come into contact with the body side as illustrated in FIG. 3. Particularly, when the attachment portions 65 are positioned on the back side of the inner member 200, the three-dimensional gathers 60 stand up so as to open outward in the width direction at and around a crotch portion, such that the three-dimensional gathers 60 come into surface contact with leg portions, and therefore the fit is improved.

Unlike the illustrated embodiment, three-dimensional gathers can be doubly (in two rows) provided on each of the left and right sides of the inner member 200.

(Absorbent Element)

The absorbent element 50 has the absorber 56 and a wrapping sheet 58 wrapping the entire absorber 56. The wrapping sheet 58 can also be omitted.

(Absorber)

The absorber 56 can be formed of an assembly of fibers. As this fiber assembly, besides those obtained by accumulating short fibers such as fluff pulp and synthetic fibers, a filament assembly obtained by opening tows (fiber bundles) of synthetic fibers such as cellulose acetate as required can also be used. When fluff pulp or short fibers are accumulated, fiber basis weight can be set to, for example, about 100 to 300 g/m$^2$, and in the case of a filament assembly, fiber basis weight can be set to about 30 to 120 g/m$^2$. In the case of a synthetic fiber, the fineness is, for example, 1 to 16 dtex, preferably 1 to 10 dtex, more preferably 1 to 5 dtex. In the case of filament assembly, the filaments may be non-crimped fibers, but are preferably crimped fibers. The degree of crimp of the crimped fiber can be, for example, about 5 to 75, preferably 10 to 50, and more preferably about 15 to 50 per inch. In addition, crimped fibers which are uniformly crimped are often used. It is preferable to disperse and hold the super absorbent polymer particles in the absorber 56.

Figure 1:
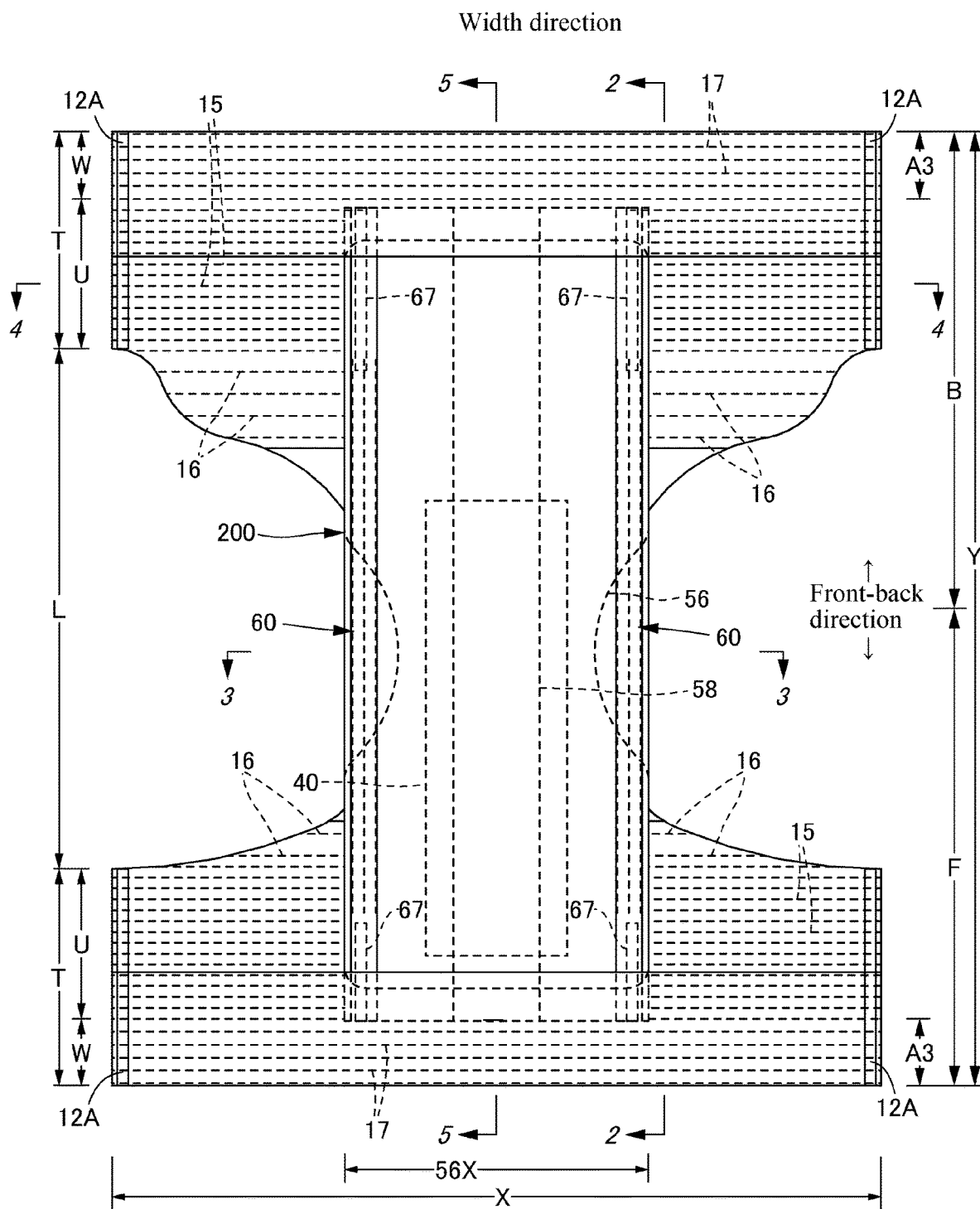
FIG. 1 is a plan view illustrating the inner surface of an underpants-type disposable diaper in a state where a diaper is spread.
Figure 2:
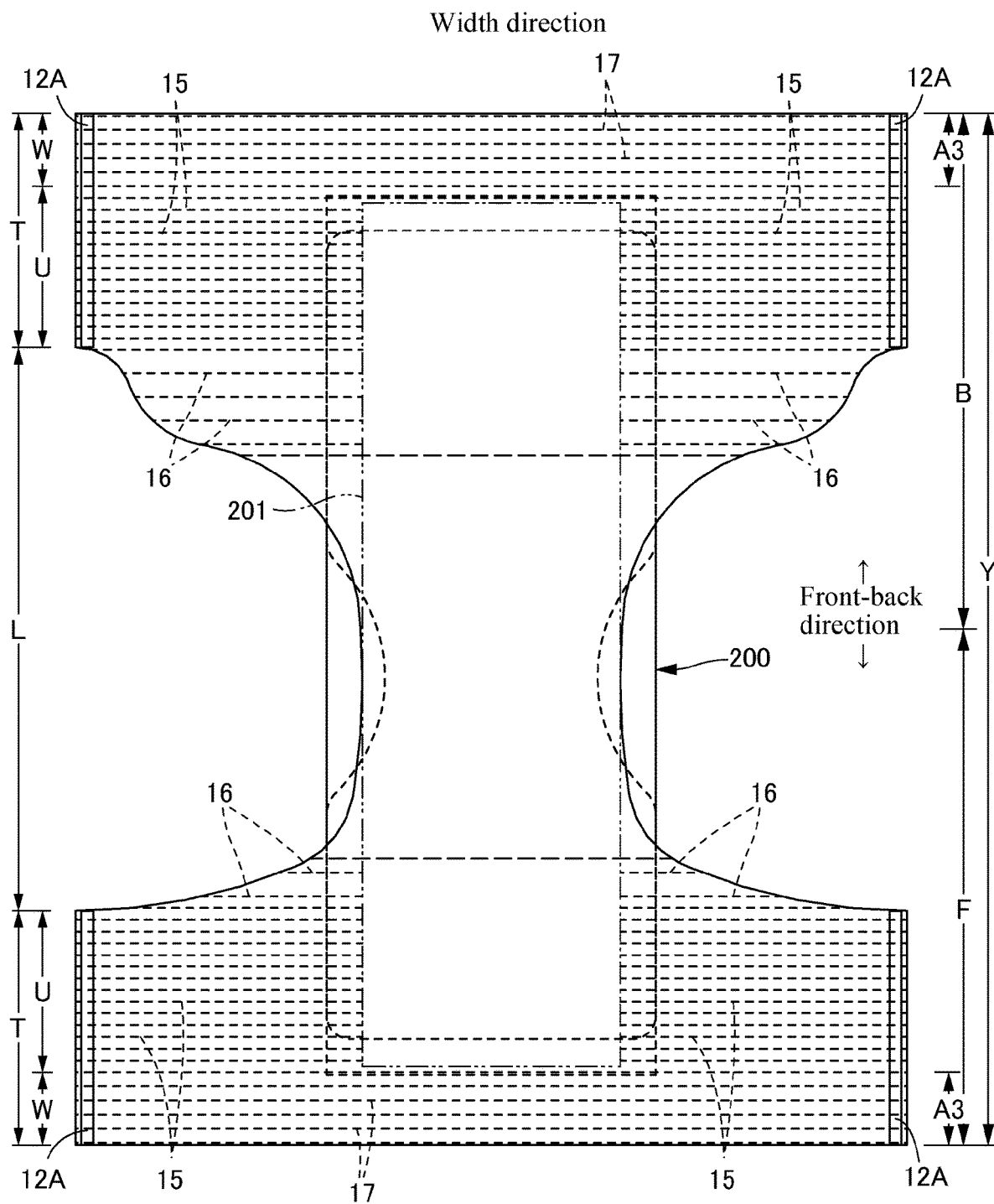
FIG. 2 is a plan view illustrating the outer surface of an underpants-type disposable diaper in a state where a diaper is spread.

The absorber 56 may have a rectangular shape, and, as illustrated in FIGS. 1 and 2, preferably has a shape similar to the outline of an hourglass where between the front end portion and the back end portion, a narrowing portion is disposed having a width smaller than that of the front end portion and that of the back end portion, since the fit of the absorber 56 and the three-dimensional gathers 60 to the legs is improved.

Further, although the size of the absorber 56 can be appropriately determined, it is preferable that the absorber 56 extends to or near the peripheral edge portion of the inner member in the front-back direction and the width direction. The reference sign 56X denotes the width of the absorber 56.

(Super Absorbent Polymer Particle)

The absorber 56 can contain super absorbent polymer particles partially or entirely. The super absorbent polymer particles include "powder" in addition to "particles". The particle sizes of super absorbent polymer particles may be those used in similar types of absorbent articles. Preferred particle sizes are desirably 1000 µm or less, in particular, 150 to 400 µm. The material of the super absorbent polymer particle is not particularly limited, but a material having a water absorption capacity of 40 g/g or more is suitable. Examples of the super absorbent polymer particle include starch-based, cellulose-based, and synthetic polymer-based particle, and starch-acrylic acid (salt) graft copolymer, saponified starch-acrylonitrile copolymer, crosslinked sodium carboxymethyl cellulose, and acrylic acid (salt) polymer. The super absorbent polymer particles have preferably a generally used particulate form. However, the super absorbent polymer particles may have another form.

The super absorbent polymer particles having a water absorption rate of 40 seconds or less are preferably used. When the water absorption rate exceeds 40 seconds, the liquid supplied into the absorber 56 tends to easily return to the outside of the absorber 56.

As the super absorbent polymer particles, those having a gel strength of 1,000 Pa or more are preferably used. This makes it possible to effectively suppress the sticky feeling after absorbing the liquid even in a bulky absorber 56.

The basis weight of the super absorbent polymer particles can be appropriately determined according to the absorption amount required for the use of the absorber 56. Therefore, although it cannot be said unconditionally, the basis weight can be 50 to 350 g/m$^2$. When the basis weight of the polymer is less than 50 g/m$^2$, it is difficult to ensure the absorption amount. When it exceeds 350 g/m$^2$, the effect is saturated.

If necessary, the super absorbent polymer particles can adjust a spraying density or a spraying amount in the planar direction of the absorber 56. For example, it is possible to increase the spraying amount in an excretory site of liquid compared to the other sites. When considering the difference between men and women, it is possible to increase the spray density (amount) on the front side for men and to increase the spray density (amount) at the center for women. Further, a portion without polymer can be provided locally (for example, in a spot shape) in the planar direction of the absorber 56.

(Wrapping Sheet)

When the wrapping sheet 58 is used, tissue paper, particularly crepe paper, nonwoven fabric, polyethylene laminated nonwoven fabric, a sheet with small openings can be used as the material. However, it is desirable that the sheet from which the super absorbent polymer particles do not come off is used. When a nonwoven fabric is used in place of crepe paper, a hydrophilic SMS nonwoven fabric (SMS, SSMMS, etc.) is particularly suitable, and polypropylene, polyethylene/polypropylene composite material and the like can be used as the material. The basis weight is desirably 5 to 40 g/m$^2$, in particular, desirably 10 to 30 g/m$^2$.

The wrapping mode of the wrapping sheet 58 can be appropriately determined. However, from the viewpoints of ease of manufacturing and prevention of leakage of super absorbent polymer particles from the front and back end edges, it is preferable that the wrapping sheet 58 is wound around in a cylindrical shape so as to surround the front and back surfaces and both side surfaces of the absorber 56, the front and back edge portions are protruded from the front and back of the absorber 56, and the protruding portions are collapsed in the thickness direction to bond by a bonding means such as a hot melt adhesive.

(Outer Member)

Figure 6:
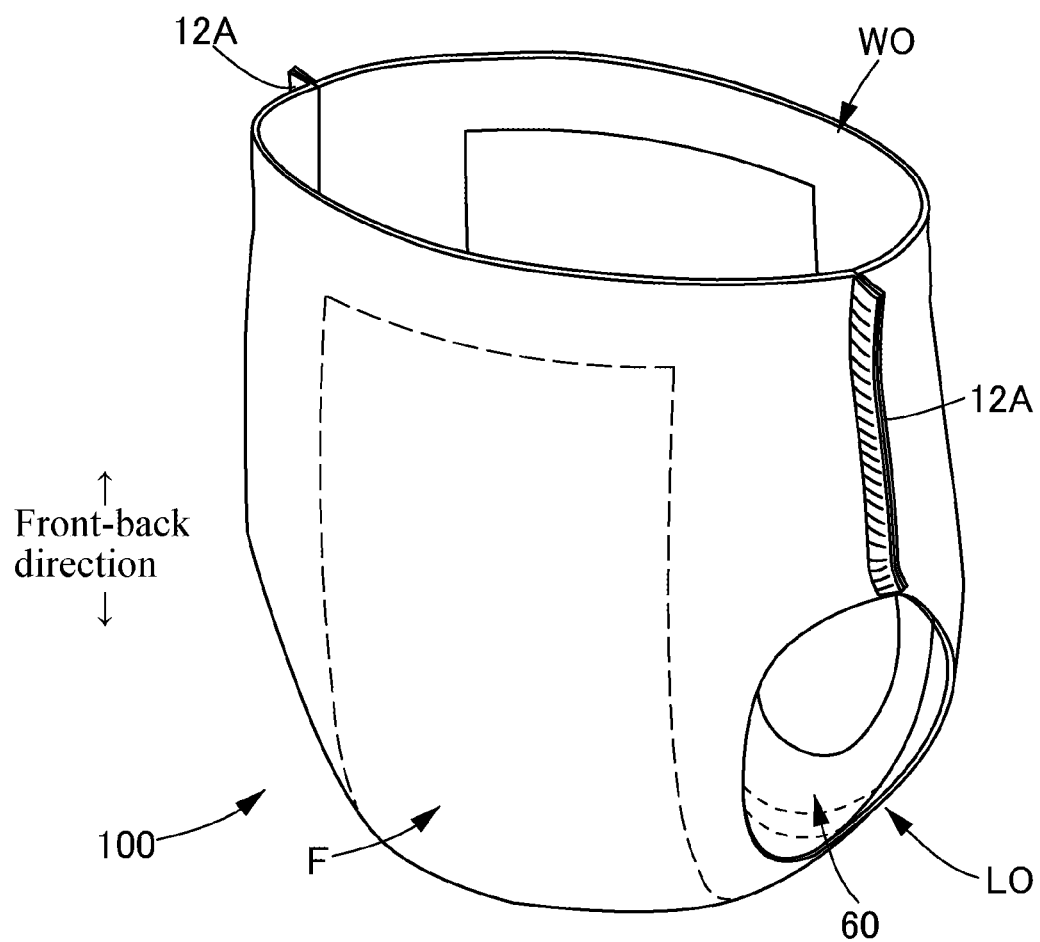
FIG. 6 is a perspective view of an underpants-type disposable diaper.

The outer member 12 has a portion disposed in a front body F extending from the center in the front-back direction to the ventral side and a portion disposed in a back body B extending from the center in the front-back direction to the dorsal side. Both side edges of the front body F and both side edges of the back body B are bonded to each other, and as illustrated in FIG. 6, a waist opening WO through which the torso of a wearer passes and a pair of left and right leg openings LO through which the legs are passed are formed. The reference sign 12A denotes a bonded side edge portion (hereinafter, this portion is also referred to as a "side seal portion"). The crotch portion means the center in the front-back direction from the waist edge of the front body F to the waist edge of the back body B in a spread state, and the front side portion and the back side portion from the center are the front body F and the back body B, respectively.

The outer member 12 has a lower torso portion T and an intermediate portion L. The lower torso portion T is defined as a range in the front-back direction from the waist opening WO to the upper ends of the leg openings LO. The intermediate portion L is defined as a range in the front-back direction of a portion forming the leg openings LO (between the region in the front-back direction having a side seal portion 12A of the front body F and the region in the front-back direction having a side seal portion 12A of the back body B). The lower torso portion T can be divided into a waist portion W which conceptually forms an edge portion of the waist opening and an under-waist portion U which is a portion lower than the waist portion W. Normally, in the lower torso portion T, in the case of having a boundary where the stretching stress along the width direction changes (for example, the fineness and stretch rate of the elastically stretchable members change), a portion nearer to the waist opening WO than a boundary closest to the waist opening WO is the waist portion W. When there is no such boundary, the waist opening WO side of the absorber 56 or the waist opening WO side of the inner member 200 is the waist portion W. The lengths of such portions in the longitudinal direction vary depending on the size of a product and can be appropriately determined. For example, the waist portion W can be set to 15 to 40 mm, and the under-waist portion U can be set to 65 to 120 mm. On the other hand, both side edges of the intermediate portion L are narrowed along the periphery of the legs of a wearer, and they are sites through which the wearer's legs pass. As a result, the outer member 12 is substantially hourglass-shaped as a whole. The degree of narrowing of the outer member 12 can be appropriately determined, and to obtain a clean appearance as in the embodiments illustrated in FIGS. 1 to 6, the narrowest portion is preferably narrower than the width of the inner member 200, but the narrowest portion may be determined to be equal to or greater than the width of the inner member 200.

As illustrated in FIGS. 3 to 5, front and back surfaces of the outer member 12 are formed by a first sheet layer 12S made of a nonwoven fabric and a second sheet layer 12H formed of a nonwoven fabric. To enhance the fit to the body, the outer member 12 has a continuous stretchable region A3, a non-stretchable region A1, and intermittent stretchable regions A2. The continuous stretchable region A3 continues in the width direction in the area nearer to the waist opening WO than to the absorber 56. The non-stretchable region A1 is provided in the middle in the width direction in the range in the front-back direction having the absorber 56. The intermittent stretchable regions A2 are provided on both sides in the width direction of the non-stretchable region A1. Between the first sheet layer 12S and the second sheet layer 12H in the continuous stretchable region A3 and the intermittent stretchable regions A2, elongated elastically stretchable members 19 (15 to 17) such as rubber threads are attached at a predetermined stretch rate along the width direction to be stretchable in the width direction (the width direction is a stretchable direction). As the elongated elastically stretchable member 19, synthetic rubber may be used, and also natural rubber may be used. The continuous stretchable region A3 may be formed over the entire width direction in a part or whole of a range in the front-back direction having the non-stretchable region A1 and the intermittent stretchable regions A2 in the illustrated embodiment. Alternatively, the range in the front-back direction of the non-stretchable region A1 in the illustrated embodiment may be extended toward the waist side or the crotch side.

To be more specific about the illustrated embodiment, the waist portion W of the outer member 12 is formed as the continuous stretchable region A3, and between the first sheet layer 12S and the second sheet layer 12H, a plurality of waist portion elastically stretchable members 17 is attached with intervals in the front-back direction in a stretched state along the width direction at a predetermined stretch rate so as to continue over the whole of the width direction. One or a plurality of the waist portion elastically stretchable members 17 disposed adjacent to the under-waist portion U may overlap with the absorber 56. A portion adjacent to the under-waist portion U in the waist portion W may be a region having the non-stretchable region A1 and the intermittent stretchable regions A2 similarly to the under-waist portion U. As the waist portion elastically stretchable members 17, about 3 to 22 rubber threads having a fineness of 155 to 1880 dtex, particularly about 470 to 1240 dtex (in the case of synthetic rubber), (in the case of natural rubber, a cross-sectional area of about 0.05 to 1.5 $mm^2$, particularly about 0.1 to 1.0 $mm^2$) are preferably attached with intervals of 5 to 20 mm, particularly 8 to 16 mm, at a stretch rate of 150 to 400%, particularly about 220 to 320%. Further, it is not necessary to make all of the waist portion elastically stretchable members 17 have the same fineness and stretch rate. For example, the fineness and the stretch rate of the elastically stretchable members 17 may be different at the upper portion and the lower portion of the waist portion W.

In addition, a plurality of under-waist portion elastically stretchable members 15 made of elongated elastically stretchable members is attached with intervals in the front-back direction in a stretched state along the width direction at a predetermined stretch rate so as to continue over the entire width direction in the upper side and both sides in the width direction of the non-stretchable region A1, except in the non-stretchable region A1, between the first sheet layer 12S and the second sheet layer 12H of the under-waist portion U of the outer member 12. As the under-waist portion elastically stretchable members 15, it is preferable that about 5 to 30 rubber threads having a fineness of 155 to 1880 dtex, particularly about 470 to 1240 dtex (in the case of synthetic rubber), (in the case of natural rubber, a cross-sectional area of about 0.05 to 1.5 $mm^2$, particularly about 0.1 to 1.0 $mm^2$) are attached with intervals of 5 to 20 mm, particularly 8 to 16 mm, at a stretch rate of 200 to 350%, particularly about 240 to 300%.

Further, a plurality of intermediate portion elastically stretchable members 16 made of elongated elastically stretchable members is attached with intervals in the front-back direction in a stretched state along the width direction at a predetermined stretch rate so as to continue over the entire width direction in the both sides in the width direction of the non-stretchable region A1, except in the non-stretchable region A1, between the first sheet layer 12S and the second sheet layer 12H of the intermediate portion L of the outer member 12. As the cover portion elastically stretchable members 16, it is preferable that about 2 to 10 rubber threads having a fineness of 155 to 1880 dtex, particularly about 470 to 1240 dtex (in the case of synthetic rubber), (in the case of natural rubber, a cross-sectional area of about 0.05 to 1.5 $mm^2$, particularly about 0.1 to 1.0 $mm^2$) are attached with intervals of 5 to 20 mm, particularly 8 to 16 mm, at a stretch rate of 150 to 300%, particularly 180 to 260%.

As with the intermittent stretchable region A2 in the illustrated embodiment, in the case where the elastically stretchable members 19 (the under-waist portion elastically stretchable members 15 and the intermediate portion elastically stretchable members 16 in the illustrated embodiment) provided in the outer member 12 are provided on both sides in the width direction of the non-stretchable region A1, except in the non-stretchable region A1, contraction of the absorber 56 in the width direction is prevented in the non-stretchable region A1. Therefore, it is preferable that the non-stretchable region A1 is the region at the intermediate region in the width direction including partly or totally a portion overlapping in the width direction with the absorber 56 (more preferably including totally the region 201 where the inner member 200 and the outer member 12 are fixed), and the intermittent stretchable regions A2 are the entire regions on both sides in the width direction of the non-stretchable region, reaching the side seal portions 12A.

(Divided Structure of Outer Member)

In the illustrated example, the outer member 12 has a structure continuously covering from the front body F to the back body B, but the outer member can have another structure where the outer member disposed in the front body F and the outer member disposed in the back body B may not be continuous but separated (not illustrated). In this case, a crotch outer member can be attached for covering the portion exposed between the outer member disposed in the front body F and the outer member disposed in the back body B on the outer surface of the inner member 200. As the crotch outer member, the same materials as those used for the outer member described above can be used.

(About Stretchable Structure)

Figure 7:
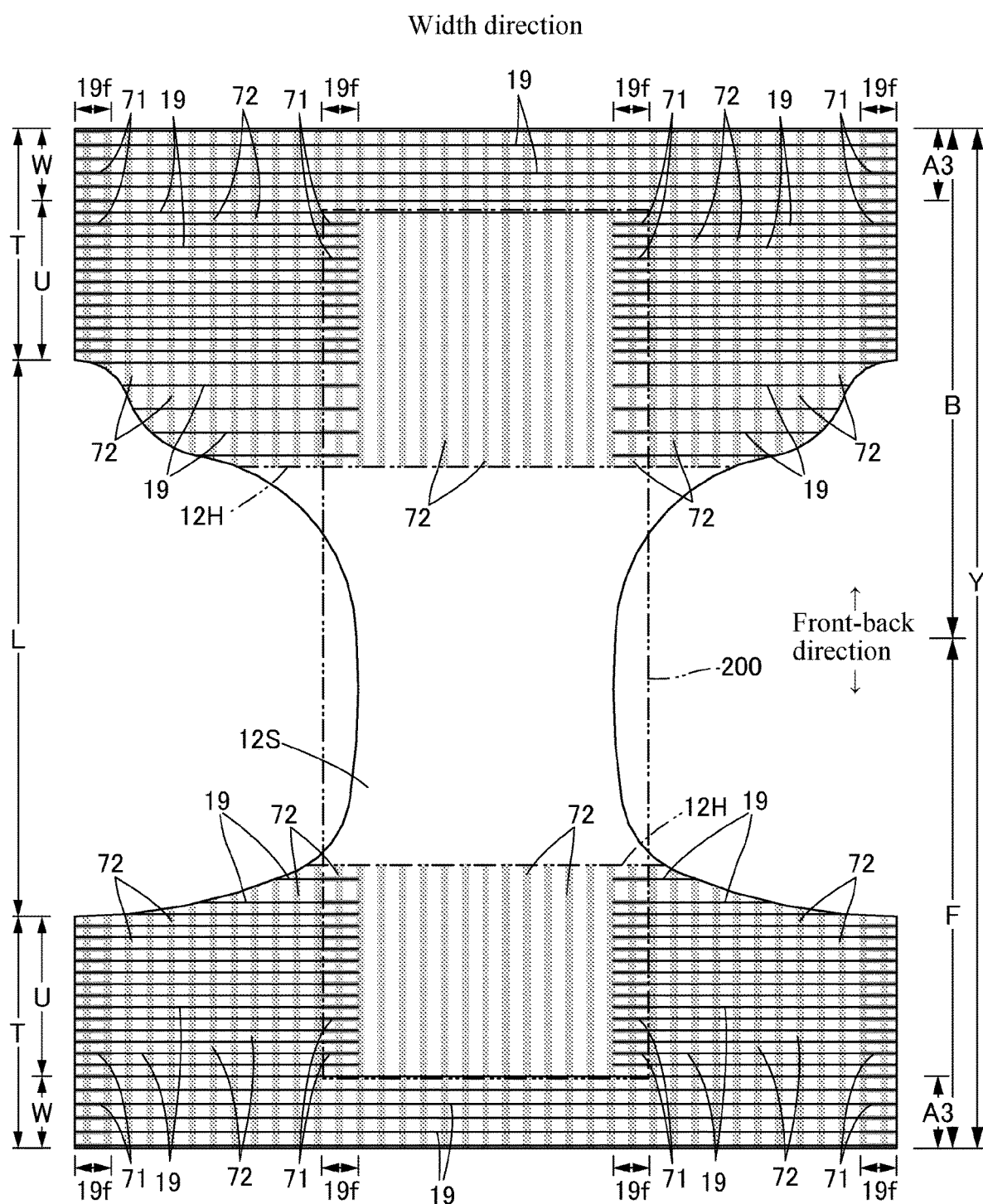
FIG. 7 is a plan view illustrating an outer member in a spread state.

In the underpants-type disposable diaper, the stretchable structure of the present invention is applied in the region from the waist portion W to the intermediate portion L. That is, as illustrated in FIGS. 4, 7, and 11, a plurality of elongated elastically stretchable members 19 is disposed with intervals from each other along the stretchable direction between the first sheet layer 12S and the second sheet layer 12H. Both end portions 19f of the elastically stretchable members 19 are fixed end portions 19f at which the elastic stretchable members are fixed to at least one of the first sheet layer 12S and the second sheet layer 12H via the first hot melt adhesive 71. The first sheet layer 12S and the second sheet layer 12H have the sheet bonded portions 70 bonded via the second hot melt adhesive 72 which is disposed in the striped pattern continuing intermittently in the longitudinal direction of the elastically stretchable members 19 and continuously elongated in the direction intersecting with the elastically stretchable members 19 in a range at least in the stretchable direction corresponding to spaces between the both end portions 19f of the elastically stretchable members 19.

(Hot Melt Adhesive)

Examples of the first hot melt adhesive 71 and the second hot melt adhesive 72 include, but are not limited to, adhesives of the EVA type, adhesive rubber type (elastomer type), olefin type, and polyester/polyamide. The first hot melt adhesive 71 and the second hot melt adhesive 72 may be the same. At the intersection positions of the second hot melt adhesive 72 and the elastically stretchable members 19, since the elastically stretchable members 19 can be fixed to at least one of the first sheet layer 12S and the second sheet layer 12H via the second hot melt adhesive 72, as long as the elastically stretchable members 19 can be sufficiently fixed only with the second hot melt adhesive 72, it is not necessary to provide the first hot melt adhesive 71.

When both of the first hot melt adhesive 71 and the second hot melt adhesive 72 are used, it is preferable that the holding power of the first hot melt adhesive 71 is higher than the holding power of the second hot melt adhesive 72. In particular, the holding power of the first hot melt adhesive 71 is preferably greater than 120 minutes, and the holding power of the second hot melt adhesive 72 is preferably 30 to 90 minutes.

Further, in general, since a hot melt adhesive having a high melt viscosity generally has the high holding power, it is desirable that the melt viscosity of the first hot melt adhesive 71 is higher than the melt viscosity of the second hot melt adhesive 72. To be more specific, the first hot melt adhesive 71 preferably has a melt viscosity of 10,000 to 40,000 mPa·s at a temperature of 140° C. and a melt viscosity of 5,000 to 10,000 mPa·s at a temperature of 160° C., and the second hot melt adhesive 72 preferably has a melt viscosity of 3,000 to 7,000 mPa·s at a temperature of 140° C. and a melt viscosity of 1,000 to 4,000 mPa·s at a temperature of 160° C.

Further, since the hot melt adhesive having high loop tack adhesive strength is suitable for bonding nonwoven fabrics to each other, it is desirable that the loop tack adhesive strength of the second hot melt adhesive 72 is higher than the loop tack adhesive strength of the first hot melt adhesive 71. Specifically, the loop tack adhesive strength of the first hot melt adhesive 71 is preferably 10 to 500 g/25 mm, and the loop tack adhesive strength of the second hot melt adhesive 72 is preferably 1,000 g/25 mm or more.

It is more preferable that the peel strength of the first hot melt adhesive 71 is 100 cN/25 mm or more in both the longitudinal and lateral directions, and the peel strength of the second hot melt adhesive 72 is 100 cN/25 mm or more in both the longitudinal and lateral directions.

The first hot melt adhesive 71 and the second hot melt adhesive 72 that satisfy such requirements can be easily obtained from hot melt adhesive manufacturers.

Although the basis weight (application amount) of the first hot melt adhesive 71 and the second hot melt adhesive 72 can be appropriately determined, it is preferable that the basis weight is in the range of 3 to 30 g/m$^2$, in particular in the range of 10 to 20 g/m$^2$.

(Fixing of Elastically Stretchable Members)

As illustrated in FIGS. 4, 7 and 11, in the elastically stretchable members 19 in the continuous stretchable region A3 and those in the intermittent stretchable region A2, the both end portions 19f in the width direction are the fixed end portions 19f fixed to the first sheet layer 12S and the second sheet layer 12H via the first hot melt adhesive 71. In the case where the elastically stretchable members 19 are provided on the both sides in the width direction of the intermediate portion in the width direction of the outer member 12, except in the intermediate portion as shown in the illustrated embodiment, the both end portions 19f of the elastically stretchable members 19 at the both sides in the width direction of the intermediate portion are defined as the fixed end portions 19f, respectively. In the case of the elastically stretchable members 19 continuing over the entire width direction of the outer member 12, the portions positioned at the both end portions 19f in the width direction of the outer member 12 of the elastically stretchable members 19 are defined as the fixed end portions 19f.

As illustrated in FIGS. 7, 8, 11 and 13, the first hot melt adhesive 71 is disposed intermittently in a direction orthogonal to the elastically stretchable members 19 and disposed only at positions overlapping with the elastically stretchable members 19. Further, as illustrated in FIGS. 9 and 15, the first hot melt adhesive 71 can be disposed in a pattern continuing in the front-back direction so as to extend over the end portions of the plurality of the elastically stretchable members 19. The first hot melt adhesive 71 may be applied to at least one of the first sheet layer 12S and the second sheet layer 12H by slot application, curtain application or the like. Further in the case of applying the first hot melt adhesive 71 only to the end portions of the elastically stretchable members 19, the first hot melt adhesive 71 may be applied only to the outer peripheral surfaces of the portions to be the both ends of the elastically stretchable members 19 by an application means such as a comb gun or a sure wrap nozzle.

Figure 8:
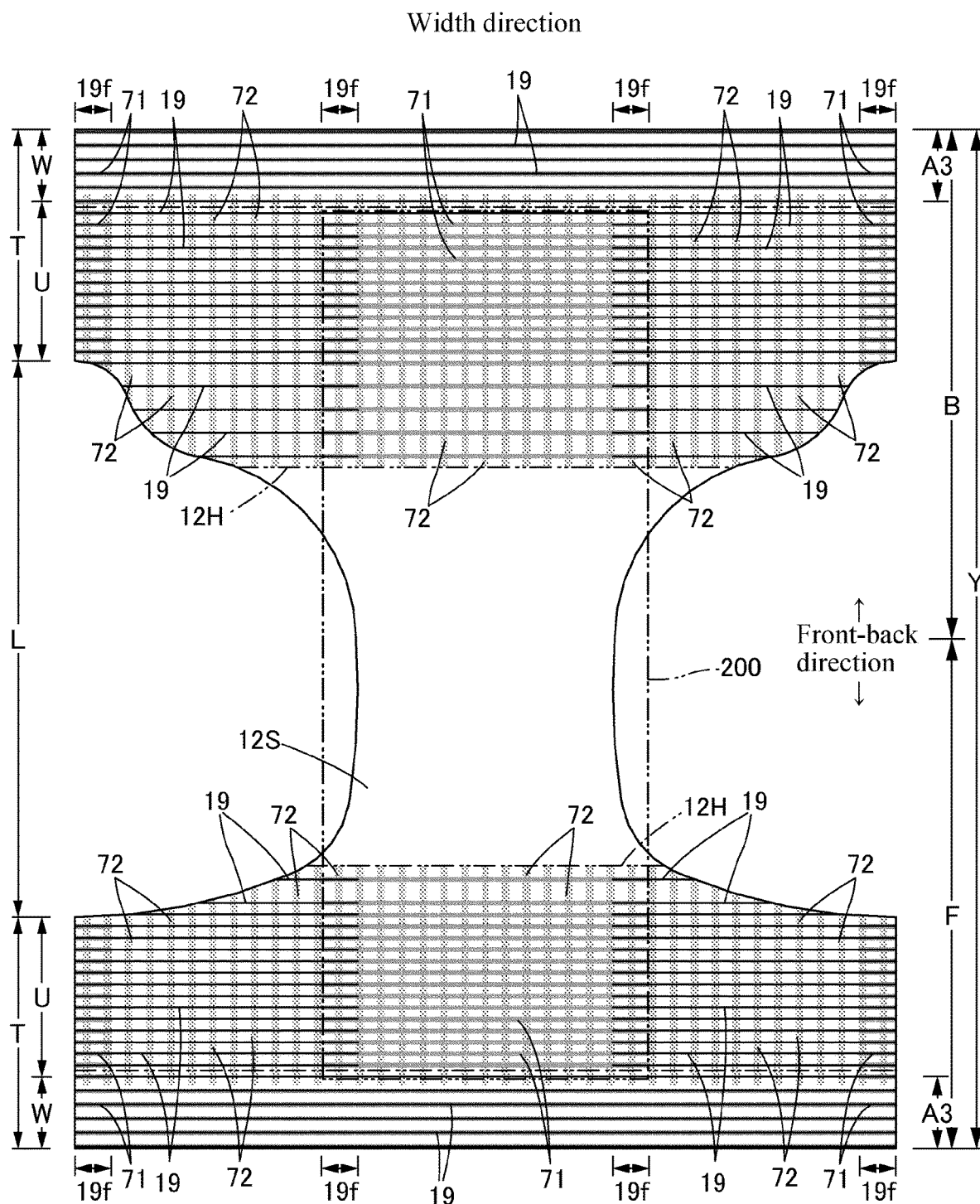
FIG. 8 is a plan view illustrating an outer member in a spread state.
Figure 9:
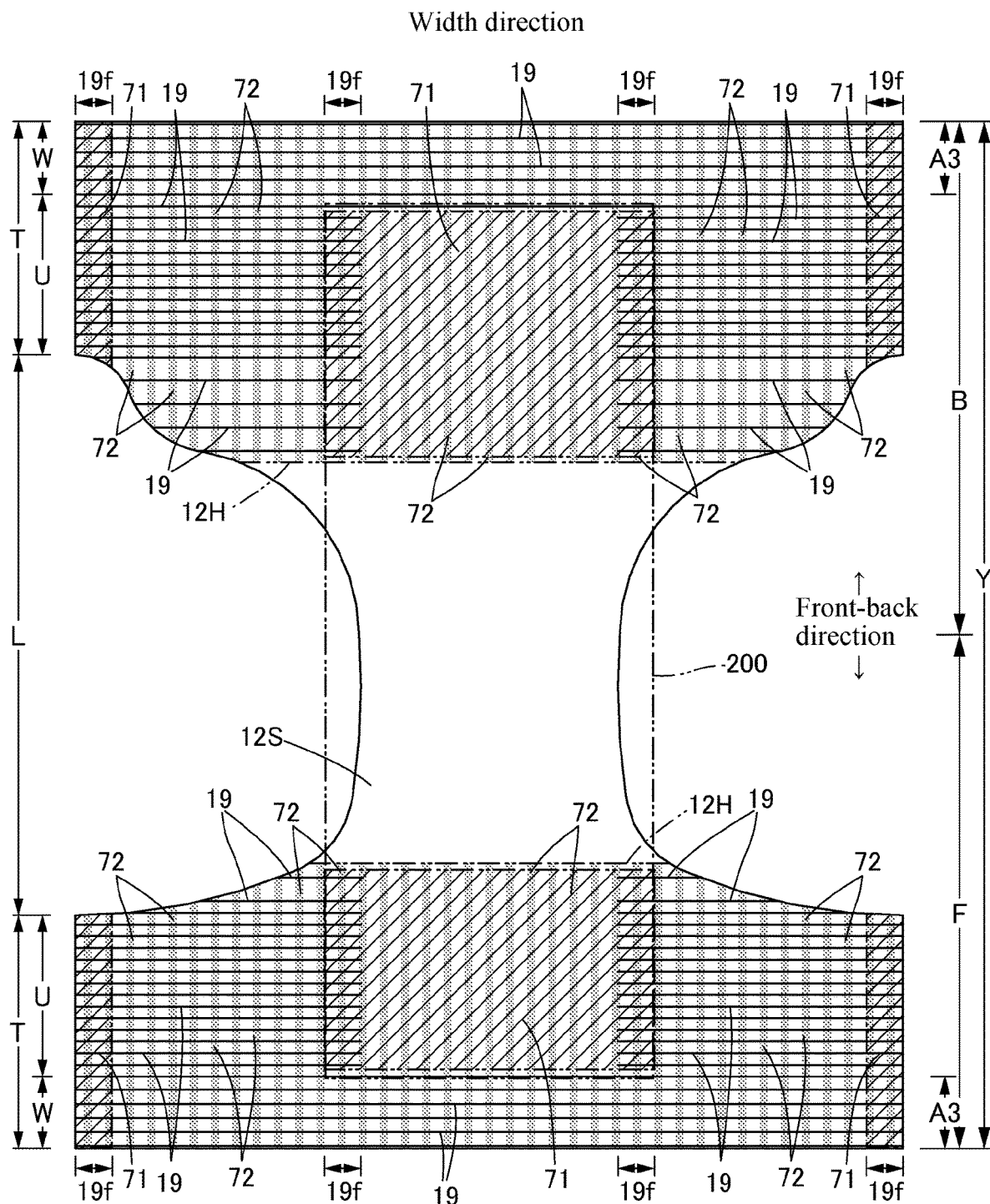
FIG. 9 is a plan view illustrating an outer member in a spread state.
Figure 10:
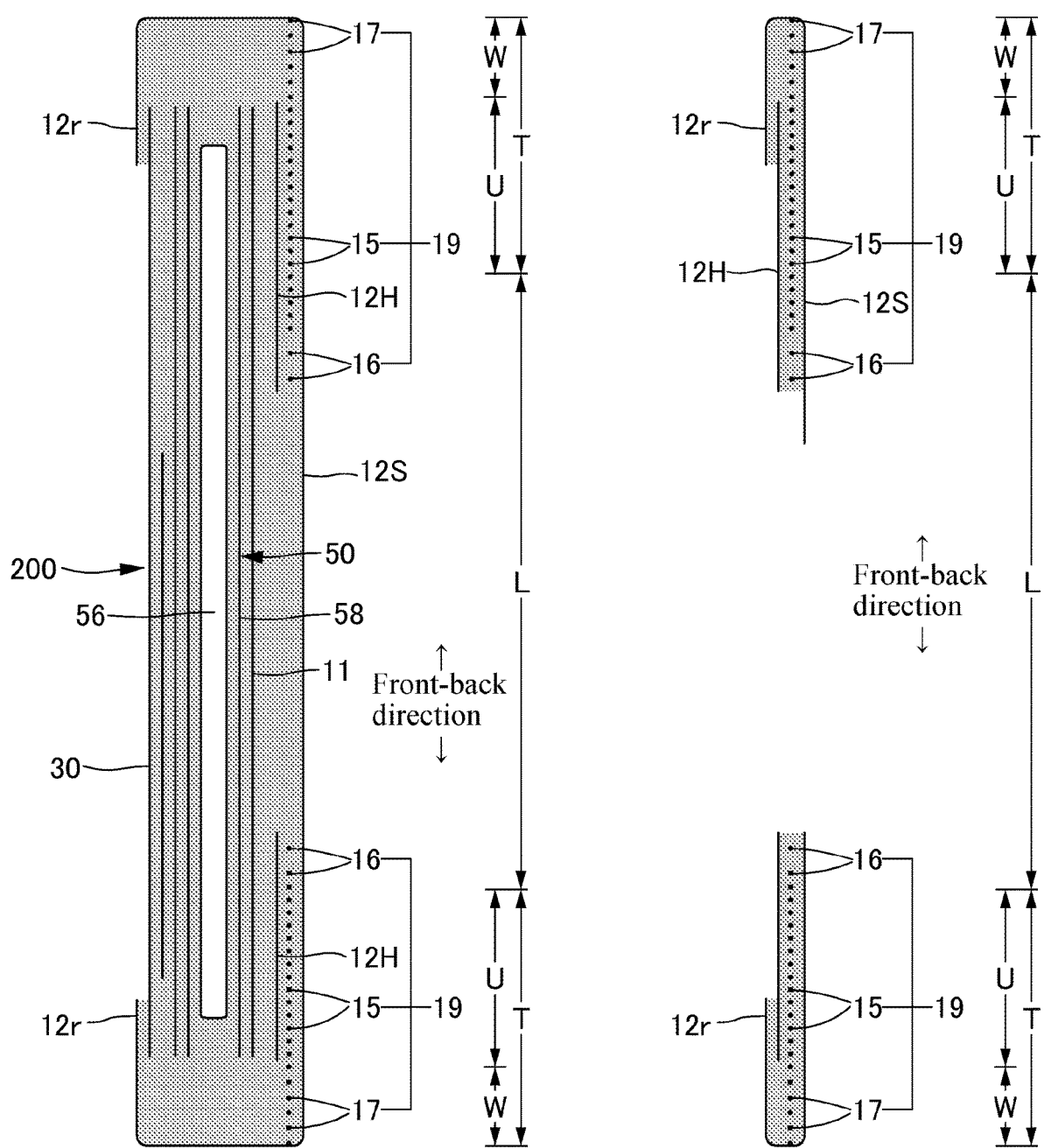
FIG. 10(a) is a cross-sectional view taken along line 5-5 in FIG. 1.
FIG. 10(b) is a cross-sectional view taken along line 2-2 in FIG. 1.

In the case of fixing the fixed end portions 19f at the center side in the width direction in the intermittent stretchable region A2, in addition to disposing the first hot melt adhesive 71 on the left and right sides individually with an interval in the width direction as illustrated in FIGS. 7 and 9, the first hot melt adhesive 71 can also be continuously disposed over the left and right fixed end portions 19f as illustrated in FIGS. 8 and 10.

Since the side seal portion 12A is a hardened portion by being welded by ultrasonic sealing or heat sealing, when the fixed end portion 19f on the side seal portion 12A side is positioned in the side seal portion 12A as illustrated in FIG. 18(a), the side seal portion 12A might become harder than necessary due to the presence of the first hot melt adhesive 71 having the high holding power, that is, having hardness. Therefore, the fixed end portion 19f on the side seal portion 12A side is preferably adjacent to the side seal portion 12A or spaced apart therefrom toward the center side in the width direction as illustrated in FIG. 18(b). As can be understood from the embodiment indicated in FIG. 18(b), it is enough that adhesion sites by the first hot melt adhesive 71 may be the end portions in the stretchable direction of the stretchable regions A2 and A3 and do not need to be the both ends of the elastically stretchable members 19 as in the illustrated embodiment. For example, ends at least at one side of the elastically stretchable members 19 are not the adhesion sites by the first hot melt adhesive 71 and the adhesion sites by the first hot melt adhesive 71 may be provided at appropriate positions near the ends of the elastically stretchable members 19.

As illustrated in FIGS. 12(d), 12(f), 12(g), 14(d), 14(g), 16(d), 16(f), and 16(g), at least a part of each adhesion site by the first hot melt adhesive 71 preferably bonds the elastically stretchable members 19 and at least one of the first sheet layer 12S and the second sheet layer 12H without using the second hot melt adhesive 72 for the following reason. Even when the holding power of the first hot melt adhesive 71 is higher than that of the second hot melt adhesive 72, in the case where the layer of the first hot melt adhesive 71 and the layer of the second hot melt adhesive 72 are interposed (in the case of double applications of adhesive) between targets to be bonded, as compared with the case where only the layer of the second hot melt adhesive 72 is interposed, the fixing force of the elastically stretchable members 19 is high, but cohesive failure of the layer is likely to occur by the interposition of the layer of the second hot melt adhesive 72, and the fixing force of the elastically stretchable members 19 is lowered.

Therefore, it is conceivable that the first hot melt adhesive 71 and the second hot melt adhesive 72 are disposed so as not to overlap each other at the passing positions of the elastically stretchable members 19 (not illustrated). However, when the positions of the first hot melt adhesive 71 and those of the second hot melt adhesive 72 are different each other as described above, it is necessary to intermittently apply the first hot melt adhesive 71 and the second hot melt adhesive 72, and accurate control of application positions of the first hot melt adhesive 71 and the second hot melt adhesive 72 is considerably difficult.

Therefore, as illustrated in FIGS. 7 to 9 and FIGS. 11 to 16, as a preferable embodiment, the second hot melt adhesive 72 is arranged with an intermittent pattern at least in the stretchable direction, the pattern includes the positions of the fixed end portions 19f of the elastically stretchable members 19 (for double applications of adhesive), and the first hot melt adhesive 71 is continuously extended in the stretchable direction with the application length longer than the application width of the second hot melt adhesive 72 at the passing positions of the elastically stretchable members 19. As a result, in the application positions of the first hot melt adhesive 71, although double application portions by the first hot melt adhesive 71 and the second hot melt adhesive 72 are partially formed, also single application portions of the first hot melt adhesive 71 are certainly formed between the application portions of the second hot melt adhesive 72. Therefore, the both end portions 19f of the elastically stretchable members 19 can be bonded via only the first hot melt adhesive 71. In this case, the continuous application width 71w of the first hot melt adhesive 71 may be appropriately determined, but it is preferably five times or more of the application width 72w of the second hot melt adhesive 72. Further, it is preferably 1.5 times or more of the interval 72d of adjacent application portions in the stretchable direction of the second hot melt adhesive 72. In a usual case, it is preferable that the total application width of the portions where the first hot melt adhesive 71 is bonded to the elastically stretchable member 19 without using the second hot melt adhesive 72 is about 5 to 30 mm. As a preferable intermittent pattern of the second hot melt adhesive 72, the bonding mode being continuous in the direction intersecting the elastically stretchable members to be described later can be exemplified.

(Sheet Bonding by Second Hot Melt Adhesive)

As long as the first sheet layer 12S and the second sheet layer 12H are bonded via the second hot melt adhesive 72 in the range at least in the width direction of the space between the fixed end portions 19f of the elastically stretchable members 19, the second hot melt adhesive 72 may be disposed in any range. However, as in the illustrated embodiment, it is preferable that the second hot melt adhesive 72 is disposed in a uniform pattern throughout the stretchable regions A2 and A3 including the fixed end portions 19f of the elastically stretchable members 19.

As illustrated in FIGS. 7 to 16, in the bonding mode being continuous in the direction intersecting the elastically stretchable members, sheet bonded portions 70 to which the first sheet layer 12S and the second sheet layer 12H are bonded via the second hot melt adhesive 72 are disposed in a striped pattern that is intermittent in the longitudinal direction of the elastically stretchable members 19 and continuous in a direction intersecting with the elastically stretchable members 19. In this bonding mode, the elastically stretchable members 19 are fixed to at least one of the first sheet layer 12S and the second sheet layer 12H at least via the first hot melt adhesive 71 in the fixed end portions 19f, whereas the elastically stretchable members 19 are fixed to at least one of the first sheet layer 12S and the second sheet layer 12H via the second hot melt adhesive 72 at intersection positions with the sheet bonded portions 70.

In this bonding mode being continuous in the direction intersecting the elastically stretchable members, along with the contraction of the elastically stretchable members 19, as illustrated in FIGS. 11(*b*), 13 (*b*), and 15 (*b*), the portions positioned between the respective sheet bonded portions 70 in the first sheet layer 12S and the second sheet layer 12H contract and are raised in the opposite directions each other to form the pleats 80. FIGS. 11(*b*), 13(*b*), and 15(*b*) indicate natural length states. The elastically stretchable members 19 are stretched from this state to a state stretched to some extent at the time of wearing, and as illustrated in FIGS. 11(*c*), 13(*c*), and 15(*c*), the hems of the pleats 80 spread. As a result, the height 80h of the pleat 80 is decreased. In addition, since this stretchable structure is in the bonding mode being continuous in the direction intersecting the elastically stretchable members, the pleats 80 extending straightly are formed along the sheet bonded portions 70, and air permeability and appearance are excellent.

In the embodiment illustrated in FIGS. 11 and 12, the adhesive 71 is applied on the surface on the second sheet layer 12H side of the first sheet layer 12S intermittently in the stretchable direction and continuously, with a predetermined width, in the direction intersecting with the stretchable direction. The adhesive 71 is not applied on the surface on the first sheet layer 12S side of the second sheet layer 12H, and the elastically stretchable members 19 are sandwiched between the first sheet layer 12S and the second sheet layer 12H in a stretched state. The first sheet layer 12S and the second sheet layer 12H as well as the first sheet layer 12S and the elastically stretchable members 19 are bonded respectively by the second hot melt adhesive 72. In this case, at the intersection portions of the sheet bonded portions 70 and the elastically stretchable members 19, since the second hot melt adhesive 72 is continuous in the direction intersecting with the stretchable direction on the first sheet layer 12S side of the elastically stretchable members 19, the elastically stretchable members 19 are fixed to the first sheet layer 12S via the second hot melt adhesive 72, whereas on the second sheet layer 12H side of the elastically stretchable members 19, the second hot melt adhesive 72 becomes discontinuous in the direction intersecting with the stretchable direction. In FIG. 12(*e*), these discontinuous portions are denoted by reference sign 73. Since the second hot melt adhesive 72 is intermittently applied in the second sheet layer 12H, a decrease in flexibility of the second sheet layer 12H, and a decrease in the flexibility as a whole of the first sheet layer 12S and the second sheet layer 12H can be suppressed. Further, at the intersection portions of the elastically stretchable members 19 and the sheet bonded portions 70, although the second hot melt adhesive 72 is continues only on the first sheet layer 12S side, on the both sides of the elastically stretchable members 19, the first sheet layer 12S and the second sheet layer 12H are bonded as one unit by the sheet bonded portions 70. Therefore, the contraction force of the elastically stretchable members 19 acts on the first sheet layer 12S and the second sheet layer 12H almost equally, and uniform pleats can be formed on both the first sheet layer 12S and the second sheet layer 12H.

It is also possible to apply the second hot melt adhesive 72 to the first sheet layer 12S and the second sheet layer 12H with the same pattern. In this case, as illustrated in FIGS. 13 and 14, since the second hot melt adhesive 72 is continuous in a predetermined width, in a direction intersecting with the stretchable direction on both the first sheet layer 12S side and the second sheet layer 12H side of the elastically stretchable members 19 at the intersection portions of the sheet bonded portions 70 and the elastically stretchable members 19, there is an advantage that the elastically stretchable members 19 can be more firmly fixed. Although not illustrated, it is also possible that the second hot melt adhesive 72 is applied to the second sheet layer 12H and not applied to the first sheet layer 12S, and the elastically stretchable members 19 are sandwiched between both the sheet layers to be bonded. However, in these modes, since the second hot melt adhesive 72 is continuous in the second sheet layer 12H, not only the deterioration of the flexibility of the second sheet layer 12H itself to be brought into contact with the skin but also the deteriorated part of the flexibility is pressed against the skin by the elastically stretchable members 19, and thus it is not preferable. Therefore, it is desirable that the second hot melt adhesive 72 is not continuous on the side having the surface that contacts the skin of a wearer like the second sheet layer 12H as shown in the embodiment indicated in FIGS. 11 and 12.

In such an embodiment, the width 70w of each sheet bonded portion 70 in the stretchable direction is preferably set to 0.5 to 4 mm (particularly 0.5 to 1 mm), and the interval 70d between the adjacent sheet bonded portions 70 is preferably set to 4 to 8 mm (particularly, 5 to 7 mm). Basically, if the width 70w of the sheet bonded portion 70 in the stretchable direction is too narrow, application of the second hot melt adhesive 72 becomes difficult, whereas if the width 70w is too wide, the flexibility reduces. Furthermore, the width 70w in the stretchable direction of each sheet bonded portion 70 affects the interval between adjacent pleats 80. As with the bonding mode being continuous in the direction intersecting the elastically stretchable members, if the pleats 80 are formed to be thin, and the width is larger than 4 mm, a space between the adjacent pleats 80 becomes too wide, and the individual pleats 80 become independent in appearance. In addition, when the pleats 80 are deformed to collapse and spread or to fall due to a compressive force in the thickness direction, the effect of mutual support of the adjacent pleats 80 is reduced. As a result, resistance with respect to the deformation and restoration after the deformation are also weaken, and the fullness becomes insufficient.

In addition, even in a case where the width 70w of the sheet bonded portion 70 in the stretchable direction is set to 0.5 to 4 mm, if the interval 70d between adjacent sheet bonded portions 70 is set to less than 4 mm or more than 8 mm, the following situation will be caused. That is, the interval 70d between adjacent sheet bonded portions 70 affects the height 80h and width of the pleats 80, and if the interval between adjacent sheet bonded portions is about 2 mm, the pleats 80 have poor continuity in the longitudinal direction as with the case of continuously fixing in the stretchable direction (it has no meaning to provide the sheet bonded portions 70 intermittently in the stretchable direction). If the interval is 3 mm, the pleats 80 are extended straightly in the direction orthogonal to the stretchable direction, but the effect of mutual support of the adjacent pleats 80 cannot be expected, and fullness becomes insufficient. In addition, when the interval 70d between the adjacent sheet bonded portions 70 exceeds 8 mm, the pleats 80 are collapsed irregularly due to the compression during wrapping, and the product appearance deteriorates. On the other hand, when the width 70w of the sheet bonded portion 70 in the stretchable direction is 0.5 to 4 mm, and at the same time, the interval 70d between the adjacent sheet bonded portions 70 is 4 to 8 mm, sufficient fullness can be finally obtained, and against the compression during wrapping, the pleats 80 are unlikely to be collapsed irregularly.

It is desirable that the width 70w of the sheet bonded portion 70 is narrow for increasing the flexibility, for example, 1 mm or less. However, due to the narrow bonded portion, it is inevitable that the fixing force of the elastically stretchable members 19 by the second hot melt adhesive 72 is reduced, and thus it is very important to fix via the first hot melt adhesive 71 having higher holding power at the fixed end portions 19f as described above.

The interval 19d between the elastically stretchable members 19 adjacent to each other can be appropriately determined. However, when the interval exceeds 10 mm, although not to the extent of the bonding mode being intermittent in the longitudinal direction, the thickness of the pleats 80 changes in a direction intersecting with the stretchable direction and causes unevenness. Therefore, in the present invention, it is preferable that the interval 19d between the adjacent elastically stretchable members 19 is 10 mm or less, particularly 3 to 7 mm.

Figure 17:
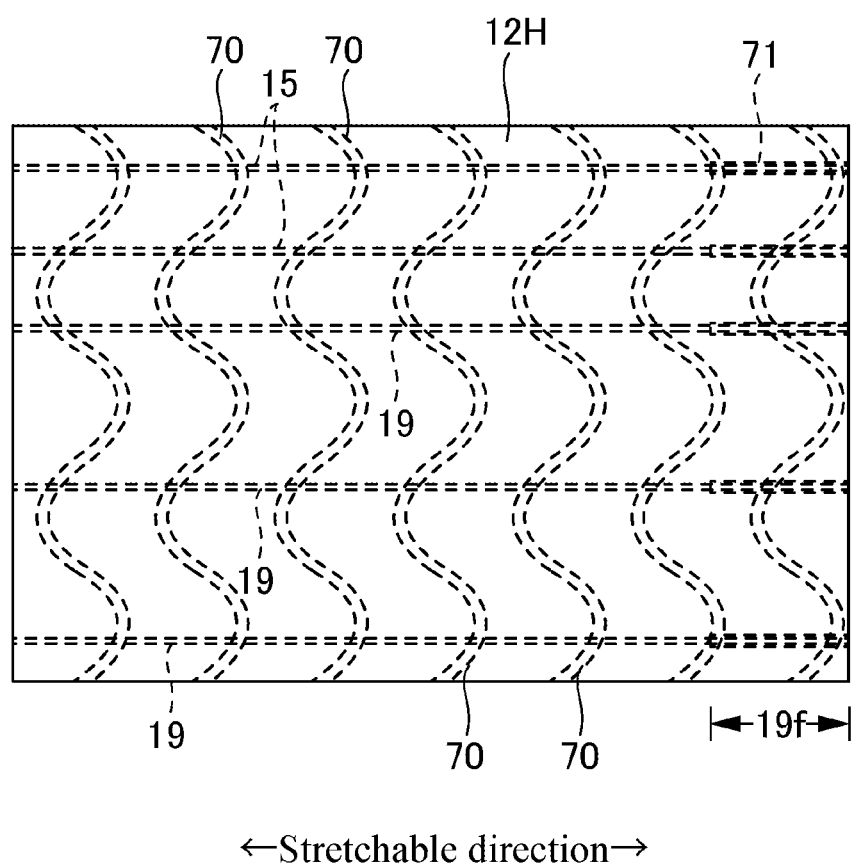
FIG. 17 is a plan view of a stretchable structure in a spread state.

The shape of the sheet bonded portion 70 (by the second hot melt adhesive 72) can be appropriately determined and may be a wave shape as illustrated in FIG. 17 or a shape extending in an oblique direction with respect to the elastically stretchable members 19, but the shape extending in a direction orthogonal to the elastically stretchable members 19 is preferable.

(Regarding the First Sheet Layer and the Second Sheet Layer)

Characteristically, either one of the first sheet layer 12S and the second sheet layer 12H is a low-adhesion nonwoven fabric having a lower peel strength with respect to the hot melt adhesive than the other sheet layer. The low-adhesion nonwoven fabric is not particularly limited, but preferably has a peel strength of 100 to 300 cN/25 mm, particularly preferably 200 to 300 cN/25 mm. The nonwoven fabric which is not a low-adhesion nonwoven fabric preferably has a peel strength of 300 cN/25 mm or more, particularly 300 to 350 cN/25 mm.

In this way, by using the low-adhesion nonwoven fabric as either one of the first sheet layer 12S and the second sheet layer 12H, even if stringiness or scattering of the hot melt adhesive occurs, under such insufficient adhesion conditions, the first sheet layer 12S and the second sheet layer 12H are not bonded or are peeled off immediately even if being bonded to some extent. Therefore, deterioration of appearance of the pleats 80, which would be caused by the unintended adhesion, is effectively prevented. In addition, both of the adhesive surfaces made of the low-adhesion nonwoven fabrics would cause a possibility that the sheet bonded portions 70 to be bonded would not be bonded sufficiently. However, in the present invention, the sheet bonded portions 70 are reliably bonded because just one adhesive surface is made of low-adhesion nonwoven fabric, and consequently, the pleats 80 excellent in appearance are formed.

It can be appropriately determined which one of the low-adhesion nonwoven fabric and the nonwoven fabric being not the low-adhesion nonwoven fabric is disposed on the outside and which one is disposed on the inside. However, from the viewpoint of hardly deteriorating the appearance of the pleats 80 on the outer surface of the product and being rich in flexibility when the outer surface of the product is touched with hand, it is desirable to dispose the low-adhesion nonwoven fabric on the outside (that is, the first sheet layer 12S in the illustrated embodiment) and to dispose the nonwoven fabric being not the low-adhesion nonwoven fabric on the inside (that is, the second sheet layer 12H in the illustrated embodiment).

The raw material fiber of the nonwoven fabric used for the first sheet layer and the second sheet layer is not particularly limited. Examples of the raw fiber include synthetic fibers such as olefin such as polyethylene and polypropylene, polyester, and polyamide, regenerated fibers such as rayon and cupra, natural fibers such as cotton, mixed fibers and composite fibers in which two or more of these are used. When flexibility is emphasized, as at least one of the first sheet layer 12S and the second sheet layer 12H, a nonwoven fabric of polypropylene (PP) or a copolymer thereof (for example, a copolymer in which polyethylene or ethylene is blended as a copolymerization component) (hereinafter also referred to as "PP type nonwoven fabric"), or a nonwoven fabric of a sheath/core fiber (PE/PP) with polyethylene (PE) as a sheath and polypropylene (PP) as a core component is preferably used.

Example of the fiber bonding structure in the nonwoven fabric include, but are not particularly limited to, spunlace, spunbond, thermalbond, meltblown, needlepunch, airthrough, and pointbond. In particular, from the viewpoints of excellent strength and flexibility, a spunbond nonwoven fabric is preferable, more particularly, a spunbond nonwoven fabric formed by laminating a plurality of spunbond layers, for example, SS nonwoven fabric (two layers) or SSS nonwoven fabric (three layers) can be suitably used, and four or more layers spunbond nonwoven fabric can also be used. The thickness and basis weight of the nonwoven fabric are not particularly limited, but it is desirable that the thickness is 0.1 to 1 mm, and the basis weight is about 10 to 20 g/m$^2$.

The nonwoven fabrics used for the first sheet layer 12S and the second sheet layer 12H may be appropriately selected from different kinds of nonwoven fabrics by measuring the peel strength thereof. However, even if the nonwoven fabrics used for the first sheet layer 12S and the second sheet layer 12H are made from the same raw material fibers and the same fiber bonding method are used for the first sheet layer 12S and the second sheet layer 12H, these nonwoven fabrics can be suitably used as a low-adhesion nonwoven fabric and a nonwoven fabric being not the low-adhesion nonwoven fabric due to the following differences between these nonwoven fabrics.

That is, for example, since heat embossing is used for fiber bonding in a spunbond nonwoven fabric, a large number of concaves are formed in a predetermined pattern on the surface of the spunbond nonwoven fabric, and alternatively, if heat embossing is performed separately for another kind of nonwoven fabric, a large number of concaves also can be formed in a predetermined pattern on the surface of the nonwoven fabric. The degree of the area rate of the concaves (the ratio of the total area of the concaves to the unit area of the nonwoven fabric) and the number of the concaves per unit area (including whether or not the concaves are formed) affect the adhesiveness of the hot melt adhesive. Specifically, as the larger the area rate of the concaves and the number of the concaves per unit area, the smaller the adhesiveness is. Therefore, nonwoven fabrics having such differences in terms of the concaves can be suitably used as the low-adhesion nonwoven fabric and the nonwoven fabric being not the low-adhesion nonwoven fabric.

Further, it has been widely practiced to add a water repellent agent to a nonwoven fabric to form a water repellent nonwoven fabric, and the difference in the content of the water repellent agent (including whether or not the water repellent agent is added) or the difference between the internal and external additions affects the adhesiveness of a hot melt adhesive. Specifically, the higher the content is, the lower the adhesiveness is, and the adhesiveness by the external addition is lower than the adhesiveness by the internal addition. Therefore, nonwoven fabrics having such differences in terms of the water repellent agent can also be suitably used as the low-adhesion nonwoven fabric and the nonwoven fabric being not the low-adhesion nonwoven fabric. As the water repellent agent, such as silicone based, paraffin based, and alkyl chromic chloride based water repellent agent can be used.

Furthermore, it has been widely practiced to add a softening agent to a nonwoven fabric, and the difference in the content of the softening agent (including whether or not the softening agent is added) or the difference between the internal and external additions affects the adhesiveness of a hot melt adhesive. Specifically, the higher the content is, the lower the adhesiveness is, and the adhesiveness by the external addition is lower than the adhesiveness by the internal addition. Therefore, nonwoven fabrics having such differences in terms of the softening agent can be suitably used as the low-adhesion nonwoven fabric and the nonwoven fabric being not the low-adhesion nonwoven fabric. As the softening agent, for example, a wax emulsion, a reactive softening agent, a silicone-based softening agent can be used, but it is preferable to use a surfactant. Examples of the surfactant include anionic surfactants such as carboxylate type anionic surfactants, sulfonate type anionic surfactants, sulfate ester type anionic surfactants, and phosphate ester type anionic surfactants (particularly alkyl phosphate); nonionic surfactants such as polyhydric alcohol mono-fatty acid esters such as sorbitan fatty acid ester, diethylene glycol monostearate, diethylene glycol monooleate, glyceryl monostearate, glyceryl monooleate, and propylene glycol monostearate, N-(3-oleyloxy-2-hydroxypropyl) diethanolamine, polyoxyethylene hydrogenated castor oil, polyoxyethylene sorbitol bees wax, polyoxyethylene sorbitan sesquistearate, polyoxyethylene monooleate, polyoxyethylene sorbitan sesquistearate, polyoxyethylene glyceryl monooleate, polyoxyethylene monostearate, polyoxyethylene monolaurate, polyoxyethylene monooleate, polyoxyethylene cetyl ether, and polyoxyethylene lauryl ether; cationic surfactants such as quaternary ammonium salts, and amine salts or amines; and amphoteric surfactant such as aliphatic derivatives of secondary or tertiary amines or aliphatic derivatives of heterocyclic secondary or tertiary amines containing carboxy, sulfonate, or sulfate.

On the other hand, as described above, when the first sheet layer 12S and the second sheet layer 12H are made of materials having different adhesiveness, in the region forming the stretchable structure according to the present invention, the first sheet layer 12S and the second sheet layer 12H are formed not by folding back one sheet material, but the first sheet layer 12S and the second sheet layer 12H are formed by using separate sheet materials, respectively. In order to form the stretchable structure of the present invention from the waist portion to the intermediate portion L, the outer member 12 of the embodiment illustrated in FIG. 5 has a first sheet material and a second sheet material, as follows. The first sheet material includes an external surface side portion extending from the edge of the waist opening WO of the front body to the edge of the waist opening of the back body and a folded portion 12r (extending so as to cover the end of the waist opening WO side of the inner member 200) folded inward at the edge of the waist opening WO of the front body. The second sheet material is bonded to the inside of the external surface side portion of the first sheet material, and extended from the waist portion W to the intermediate portion L. On the other hand, in the case where the stretchable structure of the present invention is formed from the under-waist portion U to the intermediate portion L except for the waist portion as with the embodiment illustrated in FIGS. 8 and 10, the second sheet material is not necessarily extended to the waist portion. In this case, in a range of the waist portion, the external surface side portion and the folded portion 12r of the first sheet material form the first sheet layer 12S and the second sheet layer 12H, respectively, and in a range of the under-waist portion U and the intermediate portion L, the first sheet material and the second sheet material form the first sheet layer 12S and the second sheet layer 12H, respectively. Further, it is not necessary to fold back the sheet material like the outer member 12 of the illustrated embodiments. Further, at least one of the first sheet layer 12S and the second sheet layer 12H may be partially formed of a sheet material different from that of other portions.

(Manufacturing Method)

In manufacturing, when the first hot melt adhesive 71 is used, the first hot melt adhesive 71 is applied to the elastically stretchable members 19 or the at least one of the first sheet layer 12S and the second sheet layer 12H, the second hot melt adhesive 72 is applied to at least one of the first sheet layer 12S and the second sheet layer 12H, and the elastically stretchable members 19 are sandwiched between both the sheet layers 12S and 12H at the same time when both the sheet layers 12S and 12H are bonded.

The application method of the second hot melt adhesive 72 is not particularly limited.

Figure 19:
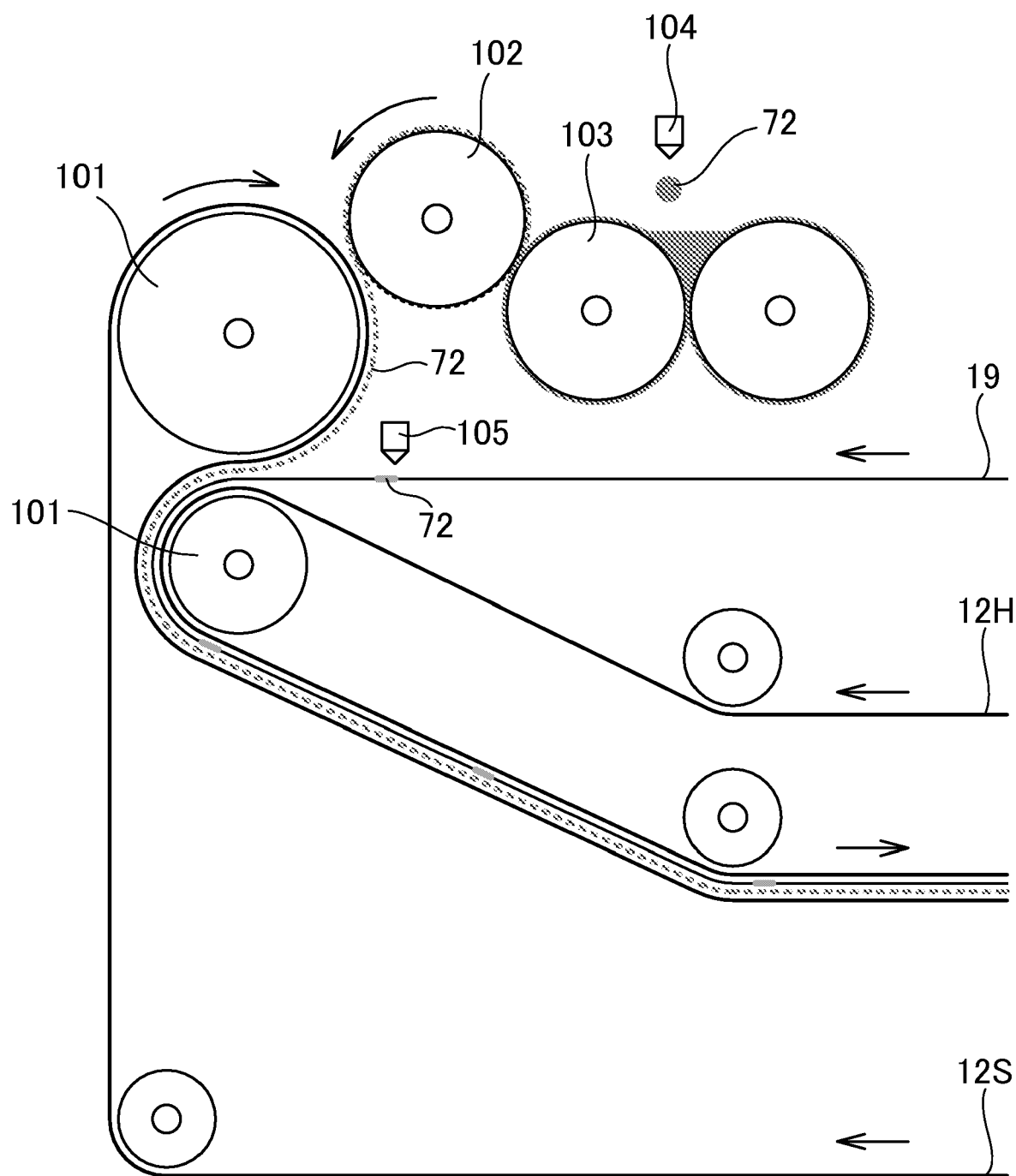
FIG. 19 is a manufacturing flow of the stretchable structure.
Figure 22:
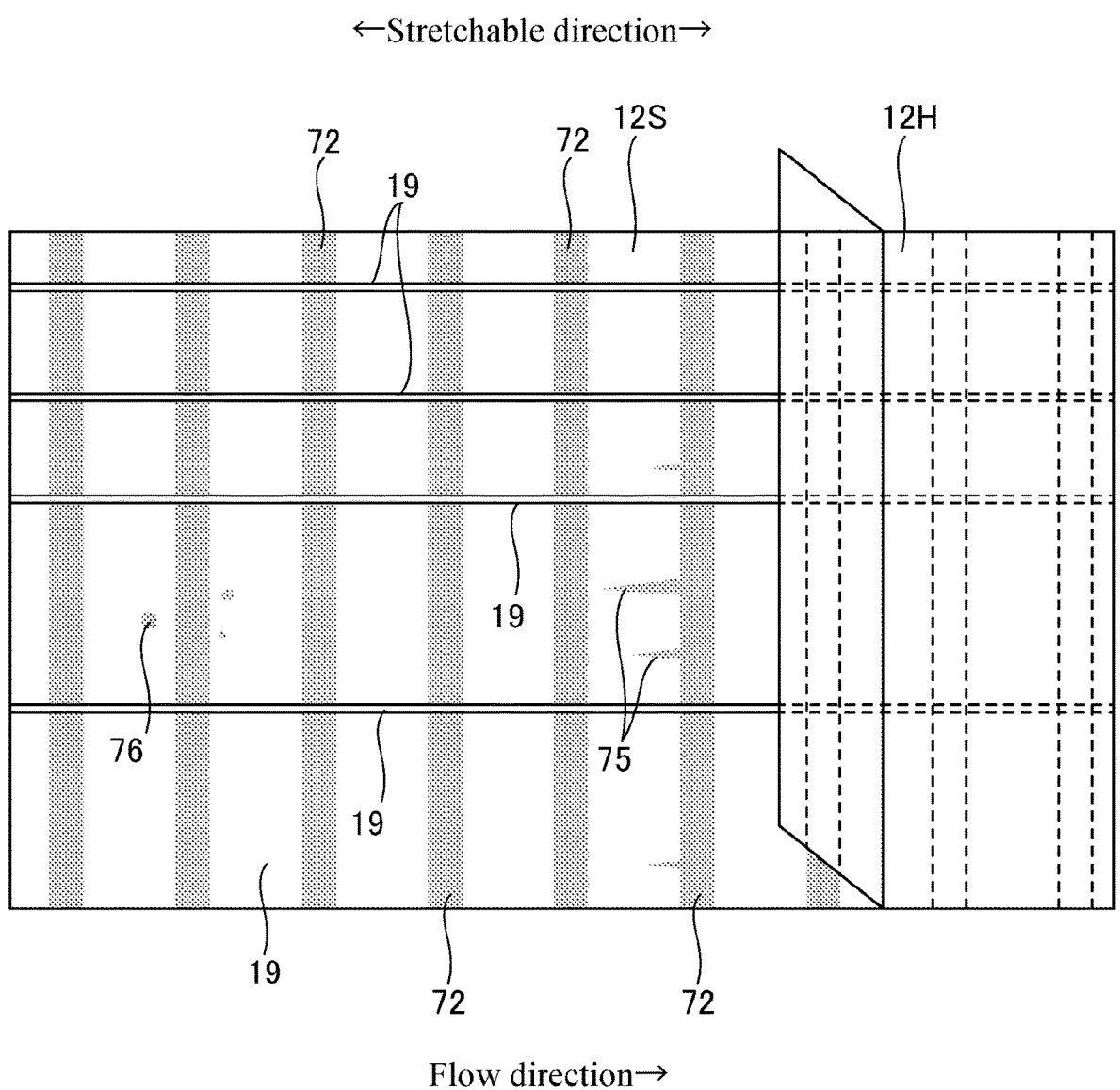
FIG. 22 is an enlarged plan view of a main part conceptually indicating stringiness and scattering of a hot melt adhesive.

However, when the width 70w of the sheet bonded portion 70 in the stretchable direction is narrow, for example, 1 mm or less, the application width of the second hot melt adhesive 72 becomes narrow, and the intermittent application by an application method, such as curtain or solid spraying from a nozzle becomes difficult. Therefore, it is desirable that a pattern coat suitable for narrow width application (transfer of the hot melt adhesive 71 in a letterpress method) is used. FIG. 19 indicates an example of a manufacturing flow using a pattern coat for applying the second hot melt adhesive 72. In this example of pattern coat type facilities, the elastically stretchable members 19 are interposed between the second sheet layer 12H and the first sheet layer 12S applied with the second hot melt adhesive 72 on the surface of the second sheet layer 12H side and fed into between a pair of nip rolls 101 so that pressure bonding is performed to form the stretchable structure illustrated in FIGS. 11 and 12. Prior to being fed into the nip rolls 101, the first sheet layer 12S is brought into contact with an engraved roll 102 having a convex pattern corresponding to the above-described sheet bonded portions 70, that is, a striped convex pattern being intermittent on the outer circumferential surface in the circumferential direction (conveying direction, machine direction: MD, a direction being the stretchable direction) and being continuous in the axial direction (direction intersecting with the conveying direction, cross direction: CD), and the second hot melt adhesive 72 held on the convex pattern of the engraved roll 102 is transferred and applied. The reference sign 103 denotes a hot melt adhesive supply roll (anilox roll in letterpress printing) for transferring and applying the second hot melt adhesive 72 to the convex pattern of the engraved roll 102 with a predetermined thickness. The reference sign 104 denotes a supply nozzle for supplying the second hot melt adhesive 72 to the hot melt adhesive supply roll 103.

In the illustrated embodiment, in order to dispose the first hot melt adhesive 71, which is applied for fixing the fixed end portions 19 of the elastically stretchable members 19, intermittently in the direction orthogonal to the elastically stretchable members 19 to overlap with the elastically stretchable members 19, the first hot melt adhesive 71 is applied intermittently in the conveying direction from a nozzle 105, which is disposed at a position where the conveyed elastically stretchable members are conveyed, to the outer peripheral surfaces of the elastically stretchable members 19, in conveying the elastically stretchable members 19, on the upstream side of a position where pressure bonding is performed. However, by an appropriate nozzle for pattern coating, spraying, curtain application or the like, the first hot melt adhesive 71 may be intermittently applied in the conveying direction to at least one of the first sheet layer 12S and the second sheet layer 12H.

(Forming of Non-Stretchable Region)

After the sheet layers 12S and 12H are bonded, and the elastically stretchable members 19 are fixed, in a region to be the non-stretchable region A1, the elastically stretchable members 19 are cut by applying pressure and heating at one or more places in the middle in the width direction, or substantially the entire elastically stretchable members 19 are finely cut by applying pressure and heating. Accordingly, the elasticity in the non-stretchable region A1 is killed while leaving elasticity in the intermittent stretchable regions A2.

FIG. 20(*a*) indicates the case where the elastically stretchable members 19 are cut at one place in the middle in the width direction. This cutting process is performed with a seal roll 80 having pressurizing portions 81 each of which is provided at one place in the circumferential direction on the outer peripheral surface of the seal roll, and each of which has a cutting convex portion 82 heated to a desired temperature, and an anvil roll 90 having a smooth surface and opposed to the seal roll 80. Then, objects to be cut, each of which includes the elastically stretchable members 19 disposed between the first sheet layer 12S and the second sheet layer 12H, are sandwiched between the seal roll 80 and the anvil roll 90. Thus, the elastically stretchable members 19 are cut by pressure and heat only at the portions nipped between the cutting convex portions 82 and the outer peripheral surface of the anvil roll 90. In products with such processing, as illustrated in FIGS. 21(*a*) and 21(*b*), between the first sheet layer 12S and the second sheet layer 12H in the non-stretchable region A1, only residual portions of the cutting continued from the elastically stretchable members 19 in the intermittent stretchable region A2 remain as idle elastically stretchable members 19r, and only one melting trace 22 remains as a cut mark. Although not illustrated, in the case of cutting at a plurality of places, the seal roll 80 having the cutting convex portions 82 at a plurality of places in the circumferential direction may be used.

Further, FIG. 20(*b*) indicates the case where almost the entire elastically stretchable members 19 are finely and almost totally cut. This cutting process is performed with a seal roll 80 having pressurizing portions 81 each of which is provided on an outer peripheral surface of the seal roll and each of which has a plurality of cutting convex portions 83 arranged in a staggered shape and the like and heated to a desired temperature. Then, objects to be cut, which include the elastically stretchable members 19 disposed between the first sheet layer 12S and the second sheet layer 12H, are sandwiched between the seal roll 80 and the anvil roll 90. Thus, the elastically stretchable members 19 are cut by pressure and heat only at the portions nipped between the cutting convex portions and the outer peripheral surface of the anvil roll 90. In the product subjected to such processing, as illustrated in FIG. 21(*c*), between the first sheet layer 12S and the second sheet layer 12H in the non-stretchable region A1, residual portions of the cutting continued from the elastically stretchable members 19 of the intermittent stretchable region A2 and the cut fragments of the elastically stretchable members separated from the elastically stretchable members 19 of both the intermittent stretchable regions A2 remain intermittently in the front-back direction and the width direction as the idle elastically stretchable members 19r, and the melting traces 22 remain intermittently in the front-back direction and the width direction as cut marks.

(Sheet Bonding in Non-Stretchable Region)

Although the sheet bonded portion 70 is not necessarily provided in the non-stretchable region A1, it is not preferable that the first sheet layer 12S is displaced or floated with respect to the second sheet layer 12H. Therefore, the first sheet layer 12S and the second sheet layer 12H are preferably bonded. Bonding of the first sheet layer 12S and the second sheet layer 12H in the non-stretchable region A1 is not particularly limited as long as the two sheet layers 12S and 12H are bonded together. However, when the bonding is performed in the above-described bonding mode being continuous in the direction intersecting the elastically stretchable members, the idle elastically stretchable members 19r in the non-stretchable region A1 are fixed to the two sheet layers 12S and 12H with the hot melt adhesive, and thus it is preferable.

From the viewpoints of ease of manufacturing and manufacturing stability, as illustrated in FIGS. 7 to 9, it is desirable that the shape, size, number, arrangement and the like of the sheet bonded portion 70 by the second hot melt adhesive 72 in the non-stretchable region A1 are the same as those of the sheet bonded portion 70 by the second hot melt adhesive 72 in the intermittent stretchable region A2. Of course, the shape, size, number, arrangement and the like of the sheet bonded portion 70 by the second hot melt adhesive 72 in the non-stretchable region A1 may be different from those of the sheet bonded portion 70 by the second hot melt adhesive 72 in the intermittent stretchable region A2.

In addition, the details of the sheet bonded portions 70 in the non-stretchable region A1 are as described in the explanation for the sheet bonded portions 70 in the stretchable region, and hence description thereof will be omitted here.

<Others>

In the examples illustrated in FIGS. 7, 9 and 10, the stretchable structure of the present invention is applied to the waist portion W, the under-waist portion U, and the intermediate portion L of the underpants-type disposable diaper. As illustrated in FIG. 8, the stretchable structure may be applied only to the under-waist portion U and the intermediate portion L (in the embodiment of FIG. 8, in the waist portion W, the elastically stretchable members 19 are fixed by the first hot melt adhesive 71 over the entire width direction). Further, it may be applied only to the under-waist portion U (particularly for example, in a case where the intermediate portion elastically stretchable member 16 is not provided). Further, the above-described stretchable structure can also be applied to other stretchable parts such as three-dimensional gathers, a lower torso portion of a dorsal side, leg portions, or fastening tapes of a tape type disposable diaper.

<Explanation of Terms Used Herein>

In the case where the following terms are used in the specification, those have the following meanings unless otherwise specified in the specification.

"Front-back (longitudinal) direction" means a direction connecting the ventral side (front side) and the dorsal side (back side). "Width direction" means a direction orthogonal to the front-back direction (right-left direction).

"Machine direction: MD" and "cross direction: CD" mean the flow direction (MD) in manufacturing facilities and the lateral direction (CD) orthogonal to the flow direction, and either one is the front-back direction, and the other is the width direction. The MD of a nonwoven fabric is the direction of fiber orientation of the nonwoven fabric. "Fiber orientation" is a direction along which a fiber of a nonwoven fabric runs and determined by, for example, a measurement method in accordance with the fiber orientation test method based on the zero span tensile strength of TAPPI T481 and a simple measurement method for determining the fiber orientation direction from the ratio of the tensile strength of the front-back direction to that of the width direction.

"Spread state" means a flatly spread state without contraction or looseness.

"Stretch rate" means the value when the natural length is taken as 100%.

"Artificial urine" is prepared by mixing urea: 2 wt %, sodium chloride: 0.8 wt %, calcium chloride dihydrate: 0.03 wt %, magnesium sulfate heptahydrate: 0.08 wt %, and ion exchanged water: 97.09 wt %, and those are used at a temperature of 40° C. unless otherwise specified.

"Gel strength" is measured as follows: 1.0 g of super absorbent polymer is added to 49.0 g of artificial urine and the mixture is stirred with a stirrer. The resulting gel is left for three hours in a thermo-hygrostat chamber at 40° C.×60% RH, and then cooled to room temperature. The gel strength of the gel is measured with a curdmeter (Curdmeter-MAX ME-500, manufactured by I. Techno Engineering Co., Ltd).

"Basis weight" is measured as follows. After preliminary drying a sample or a test piece, the sample or the test piece is left in a test room or apparatus under normal conditions (the test location is at a temperature of 20±5° C. and with a relative humidity of 65% or less) to be constant weight. The preliminary drying is to make a sample or a test piece be constant weight in an environment having a temperature of not exceeding 50° C. and a relative humidity of 10 to 25%. For fibers with an official moisture regain of 0.0%, preliminary drying may not be performed. A sample of dimensions (200 mm×250 mm±2 mm) is cut using a cutting template (200 mm×250 mm, ±2 mm) from a test piece in a constant weight. The basis weight is set by weighing the sample, multiplying by 20, and calculating the weight per one square meter.

"Thickness" is automatically measured under the conditions of a load of 10 gf/cm² and a pressing area of 2 cm² using an automatic thickness measuring device (KES-G5 handy compression tester).

"Water absorption capacity" is measured according to JIS K7223-1996 "Testing method for water absorption capacity of super absorbent polymers".

"Water absorption rate" is the "time to end point" when JIS K7224-1996 "Testing method for water absorption rate of super absorbent polymers" has been carried out using 2 g of super absorbent polymers and 50 g of physiological saline solution.

Figure 23:
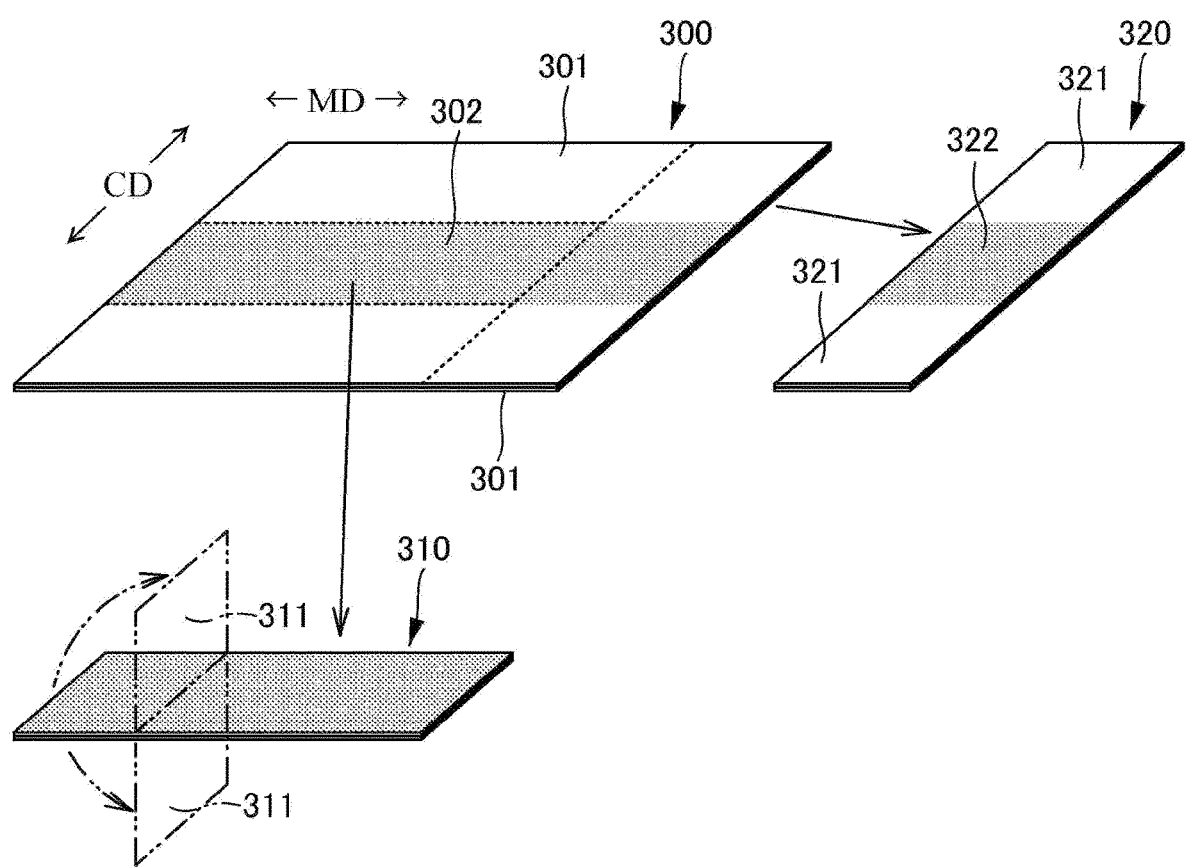
FIG. 23 is an explanatory view of a test piece of a peel strength measurement test.
Figure 24:
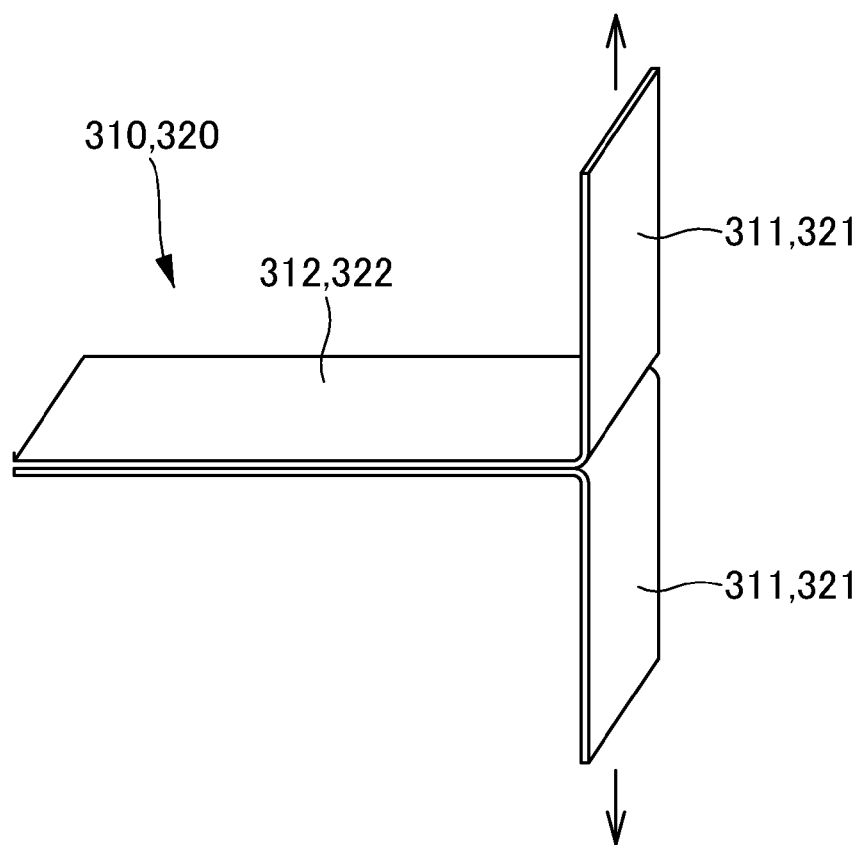
FIG. 24 is an explanatory view of a peel strength measurement test.

"Peel strength" of the hot melt adhesive is measured as follows. That is, two hydrophobic spunbond nonwoven fabrics 301 composed of PP fibers having the fineness of 1.44 dtex and a basis weight of 17 g/m² are prepared (MD 100 mm or more×CD 75 mm or more). The hot melt adhesive 302 to be measured is applied with the application amount of 20 g/m² continuously in the MD with the application width of 25 mm in a center region in the CD of one nonwoven fabric 301. To this nonwoven fabric 301, the other nonwoven fabric 301 is bonded via the hot melt adhesive 302 so that they are aligned in the MD and the CD. Subsequently, a nonwoven fabric adhesive body 300 illustrated in FIG. 23 is obtained by the pressure bonding where a 2 kg roller is rolled back and forth once. Next, from this nonwoven fabric adhesive body 300, a longitudinal direction test piece 310 and a lateral direction test piece 320 are prepared by cutting along the cutting lines indicated by dotted lines in FIG. 23 so that the longitudinal direction test piece 310 of 75 mm in the MD×25 mm in the CD is entirely bonded and the lateral direction test piece 320 has non-adhesive portions 321 at both sides thereof of 25 mm from both ends in the CD and adhesive portion 322 of 25 mm in the MD×25 mm in the CD provided between the non-adhesive portions 321. In the longitudinal direction test piece 310, as indicated by two-dot chain lines in FIG. 23, both nonwoven fabrics at one side thereof of 25 mm from one end in the MD are peeled off (adhesive force of an object to be bonded is lowered by cooling the object with a cold spray) to form grip margins 311. The grip margins 311 of nonwoven fabrics are gripped with the upper and lower grips of a tensile tester under the conditions of a grip interval of 30 mm and a test speed of 300 mm/min, and as illustrated in FIG. 24, the remaining adhesive portion 312 is peeled off, and the force (cN/25 mm) required for peeling is measured. In the lateral direction test piece 320, a test is performed in the same manner as the longitudinal direction test piece 310, except that nonwoven fabrics of the non-adhesive portions 321 at both ends in the CD are grasped by the upper and lower grips of the tensile tester. Then, the failure state of a peeled portion is monitored, and at the time of interfacial failure (interfacial peeling) and cohesive failure, the average value of force at each point is taken as a measurement value by choosing first five peaks and first five bottom points from a corrugated portion after the start of peeling (after the curve has risen) in the measurement curve with the vertical axis as the force. Further, at the time of the material failure (failure of the base material), the maximum value of the force is taken as the measurement value. The above measurements are performed three times for each of the longitudinal direction test piece 310 and the lateral direction test piece 320, and the measured values of three times are averaged to obtain the longitudinal peel strength and the lateral peel strength.

Figure 25:
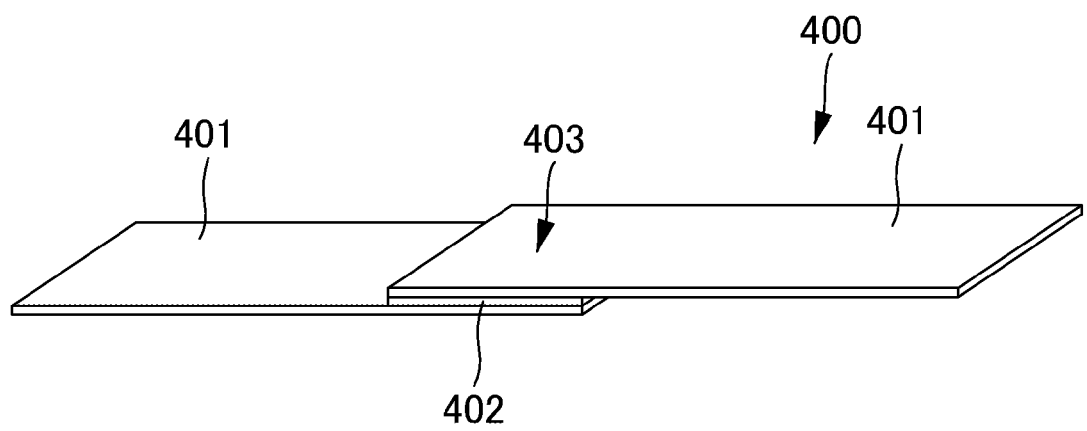
FIG. 25 is an explanatory view of a test piece of a holding power measurement test.
Figure 26:
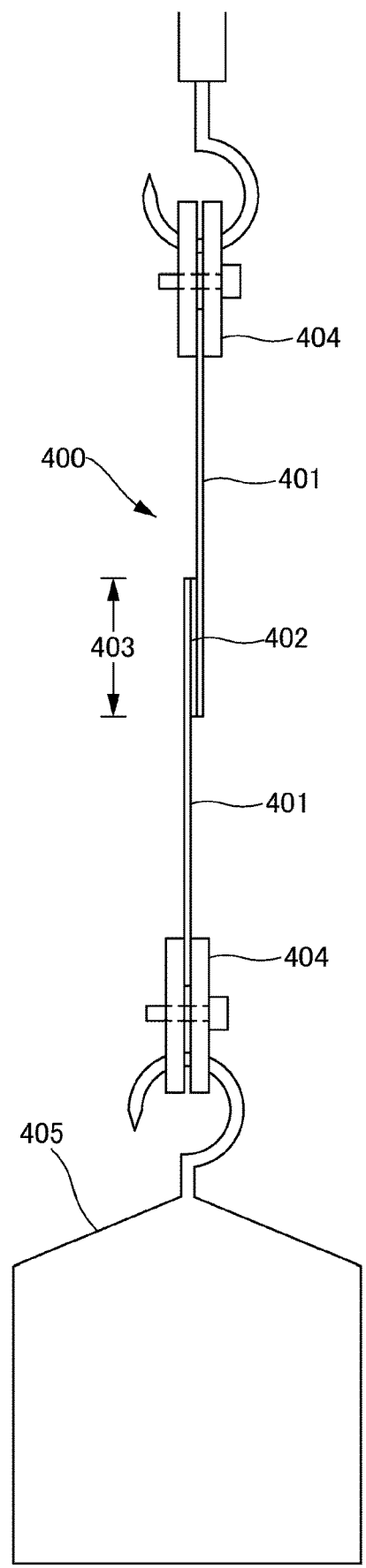
FIG. 26 is an explanatory view of a holding power measurement test.

"Holding power" of the hot melt adhesive is measured as follows. That is, as illustrated in FIG. 25, a PET film having a thickness of 25 μm is cut into two rectangular PET films 401 having a length of 100 mm×a width of 25 mm, and the end portions in the longitudinal direction of the PET films (25 mm from one end in the longitudinal direction) are adhered to each other via the hot melt adhesive layer 402 to be measured, to prepare a test piece 400. The adhesive portion 403 of the test piece 400 is 25 mm×25 mm. The hot melt adhesive layer 402 is applied by slot application at a thickness of 20 g/m², and after bonding, a 2 kg roller is rolled back and forth once over the adhesive portion 403 for pressure bonding. Then the test piece 400 is left under the room temperature (23° C.) for 16 hours. Further, as illustrated in FIG. 26, the both end portions of the test piece or the PET film 401 are clamped with upper and lower grips 404 tightened with screws in the thickness direction, and left in a creep tester (thermostatic chamber) for two hours at 40° C. so that a force is not applied to the adhesive portion 403. Subsequently, in the creep tester, as illustrated in FIG. 26, the upper one of the grips 404 is suspended, and a weight 405 is suspended from the lower one of the grips 404. A vertical load of one kilogram in total (the sum of the weight 405 and the weight-side grip 405) is applied to the sample. The time from the start of application of load to the complete separation of the adhesive portion 403 or of the PET film on the side of the weight 405 is measured. The time is measured up to 120 minutes, and when the weight does not fall before 120 minutes, the measurement result is "over 120 minutes". The above measurement is performed three times, and the average value of the measurement results is taken as the holding power (minute). As a result of three measurements, when one result is over 120 minutes and two results are 120 minutes or less, the average value of the two measurement results of 120 minutes or less is used as the holding power. When two results are more than 120 minutes and one result is 120 minutes or less, the one measurement result of 120 minutes or less is taken as the holding power. When three results are over 120 minutes, the holding power is over 120 minutes.

"Loop tack adhesive strength" means a value measured as follows. That is, a hot melt adhesive is applied at a thickness of 50 μm on a 50 μm-thick PET plate. This PET plate is cut into a strip having a size of 25 mm in width and 125 mm in length. Two ends of the strip are overlapped to form a loop. After fixing this loop to the LT-100 type loop tack tester (manufactured by Cheminstruments Inc.), the loop is bonded to a PE (polyethylene) plate in an adhesion area of 25 mm×25 mm for an adhesion time of two seconds. Next, the loop is peeled off at 20° C. at a speed of 300 mm/min, and the maximum force is measured as the loop tack adhesive strength.

"Melt viscosity" is measured at a prescribed temperature using a Brookfield B type viscometer (spindle No. 027) in accordance with JIS Z 8803.

When environmental conditions in tests and measurements are not described, the tests and measurements shall be carried out in a test room or apparatus under normal conditions (the test location is at a temperature of 20±5° C. and with a relative humidity of 65% or less).

The dimensions of each part are measured in the spread state, not the natural length state, unless otherwise stated.

INDUSTRIAL APPLICABILITY

The present invention can be applied to a stretchable structure and a manufacturing method therefor preferably in an underpants-type disposable diaper as in the above example, and also in a general absorbent article such as a disposable diaper of a tape type or a pad type as well as a sanitary napkin.

REFERENCE SIGNS LIST 11 liquid impervious sheet
12 outer member
12A side seal portion
12H second sheet layer
12S first sheet layer
12r folded portion
19 elastically stretchable member
30 top sheet
40 intermediate sheet
50 absorbent element
56 absorber
58 wrapping sheet
60 three-dimensional gather
62 gather sheet
70 sheet bonded portion
71 first hot melt adhesive
72 second hot melt adhesive
80 pleat
200 inner member

The invention claimed is:

1. A stretchable structure of an absorbent article, comprising:
a first sheet layer made of a nonwoven fabric;
a second sheet layer made of a nonwoven fabric and opposed to one side surface of the first sheet layer; and
a plurality of elongated elastically stretchable members provided along a stretchable direction at intervals from each other between the first sheet layer and the second sheet layer,
wherein the first sheet layer and the second sheet layer have sheet bonded portions bonded via a hot melt adhesive disposed in a striped pattern that is intermittent in a longitudinal direction of the elastically stretchable members and continuously elongated in a direction intersecting with the elastically stretchable members;
wherein the first sheet layer is made of a low-adhesion nonwoven fabric having a lower peel strength with respect to the hot melt adhesive than the second sheet layer;
wherein the elastically stretchable members have a first side facing the first sheet layer and a second side facing the second sheet layer;
wherein at intersection points of the sheet bonded portions and the elastically stretchable members, the hot melt adhesive is discontinuous in the direction intersecting with the elastically stretchable members on the first side and continuous in the direction intersecting with the elastically stretchable members on the second side.

2. The stretchable structure of an absorbent article according to claim 1, wherein the hot melt adhesive has a melt viscosity of 10,000 to 40,000 mPa·s at a temperature of 140° C., a melt viscosity of 5,000 to 10,000 mPa·s at a temperature of 160° C., and a loop tack adhesive strength of 10 to 500 g/25 mm.

3. The stretchable structure of an absorbent article according to claim 1, wherein a width of each sheet bonded portion in the stretchable direction is 0.5 to 4 mm, and an interval between adjacent sheet bonded portions is 4 to 8 mm.

4. A stretchable structure of an absorbent article, comprising:
a first sheet layer made of a nonwoven fabric;
a second sheet layer made of a nonwoven fabric and opposed to one side surface of the first sheet layer; and
a plurality of elongated elastically stretchable members provided along a stretchable direction at intervals from each other between the first sheet layer and the second sheet layer,
wherein the first sheet layer and the second sheet layer have sheet bonded portions bonded via a hot melt adhesive disposed in a striped pattern that is intermittent in a longitudinal direction of the elastically stretchable members and continuously elongated in a direction intersecting with the elastically stretchable members; and
wherein the first sheet layer is made of a low-adhesion nonwoven fabric having a lower peel strength with respect to the hot melt adhesive, a higher area rate of concaves, and a larger number of concaves per unit area than the second sheet layer.

5. A stretchable structure of an absorbent article, comprising:
a first sheet layer made of a nonwoven fabric;
a second sheet layer made of a nonwoven fabric and opposed to one side surface of the first sheet layer; and
a plurality of elongated elastically stretchable members provided along a stretchable direction at intervals from each other between the first sheet layer and the second sheet layer,
wherein the first sheet layer and the second sheet layer have sheet bonded portions bonded via a hot melt adhesive disposed in a striped pattern that is intermittent in a longitudinal direction of the elastically stretchable members and continuously elongated in a direction intersecting with the elastically stretchable members;
wherein the first sheet layer is made of a low-adhesion nonwoven fabric having a lower peel strength with respect to the hot melt adhesive than the second sheet layer; and
wherein the low-adhesion nonwoven fabric of the first sheet layer has a higher content of a water repellent agent than the nonwoven fabric of the second sheet layer, or the water repellent agent is externally added to the low-adhesion nonwoven fabric of the first sheet layer and the water repellent agent is internally added to the nonwoven fabric of the second sheet layer.

6. A stretchable structure of an absorbent article, comprising:
a first sheet layer made of a nonwoven fabric;
a second sheet layer made of a nonwoven fabric and opposed to one side surface of the first sheet layer; and
a plurality of elongated elastically stretchable members provided along a stretchable direction at intervals from each other between the first sheet layer and the second sheet layer,
wherein the first sheet layer and the second sheet layer have sheet bonded portions bonded via a hot melt adhesive disposed in a striped pattern that is intermittent in a longitudinal direction of the elastically stretchable members and continuously elongated in a direction intersecting with the elastically stretchable members;
wherein the first sheet layer is made of a low-adhesion nonwoven fabric having a lower peel strength with respect to the hot melt adhesive than the second sheet layer; and
wherein the low-adhesion nonwoven fabric of the first sheet layer has a higher content of a softening agent than the nonwoven fabric of the second sheet layer, or the softening agent is externally added to the low-adhesion nonwoven fabric of the first sheet layer and the softening agent is internally added to the nonwoven fabric of the second sheet layer.

7. The stretchable structure of an absorbent article according to claim 1,
wherein the absorbent article is an underpants-type disposable diaper, in which an outer member disposed in a front body and a back body and an inner member attached to the outer member and including an absorber are provided;
wherein both side edges of the outer member of the front body and both side edges of the outer member of the back body are bonded to each other;
wherein a range corresponding in a front-back direction to the bonded side edges is an annular lower torso portion, and a waist opening and a pair of right and left leg openings are formed;
wherein the stretchable structure is provided in a region of the outer member located on both sides of the inner member in a width direction such that the elastically stretchable members extend along the width direction; and
wherein the low-adhesion nonwoven fabric of the first sheet layer is located facing outwardly from a skin surface of a wearer, and the nonwoven fabric of the second sheet layer is located facing inwardly toward the skin surface of the wearer.

8. A method of manufacturing a stretchable structure of an absorbent article, comprising:
using a first sheet layer and a second sheet layer, wherein the first sheet layer is made of a low-adhesion nonwoven fabric having a lower peel strength with respect to a hot melt adhesive than the second sheet layer;
sandwiching a plurality of elongated elastically stretchable members provided along a stretchable direction at intervals from each other between the first sheet layer and the second sheet layer; and
forming sheet bonded portions by bonding the first sheet layer and the second sheet layer via the hot melt adhesive disposed in a striped pattern that is intermittent in a longitudinal direction of the elastically stretchable members and continuously elongated in a direction intersecting with the elastically stretchable members;
wherein forming the sheet bonded portions comprises applying the hot melt adhesive to the second sheet layer and not applying the hot melt adhesive to the first sheet layer.

9. The method of manufacturing the stretchable structure of an absorbent article according to claim 8,
wherein the hot melt adhesive has a melt viscosity of 10,000 to 40,000 mPa·s at a temperature of 140° C., a melt viscosity of 5,000 to 10,000 mPa·s at a temperature of 160° C., and a loop tack adhesive strength of 10 to 500 g/25 mm.

10. A method of manufacturing the stretchable structure of an absorbent article, comprising:
using a first sheet layer and a second sheet layer, wherein the first sheet layer is made of a low-adhesion nonwoven fabric having a lower peel strength with respect to a hot melt adhesive than the second sheet layer;
sandwiching a plurality of elongated elastically stretchable members provided along a stretchable direction at intervals from each other between the first sheet layer and the second sheet layer; and
forming sheet bonded portions by bonding the first sheet layer and the second sheet layer via the hot melt adhesive disposed in a striped pattern that is intermittent in a longitudinal direction of the elastically stretchable members and continuously elongated in a direction intersecting with the elastically stretchable members;
a step of applying the hot melt adhesive, in which at least one of the first sheet layer and the second sheet layer is brought into contact with an engraved roll such that a circumferential direction of the engraved roll is a stretchable direction, and the hot melt adhesive, which is held in the striped pattern that is intermittent in the circumferential direction and continuous in an axial direction on the outer peripheral surface of the engraved roll, is transferred on at least one of the first sheet layer and the second sheet layer; and
a step of performing pressure bonding, in which the elastically stretchable members are sandwiched between the first sheet layer and the second sheet layer, on at least one of which the hot melt adhesive is transferred,
wherein in the step of applying the hot melt adhesive, on the outer peripheral surface of the engraved roll, an application width in the circumferential direction of the hot melt adhesive is set to 0.5 to 4 mm, and an interval between the adjacent applications in the circumferential direction of the hot melt adhesive is set to 4 to 8 mm.

11. A method of manufacturing the stretchable structure of an absorbent article, comprising:
using a first sheet layer and a second sheet layer, wherein the first sheet layer is made of a low-adhesion nonwoven fabric having a lower peel strength with respect to a hot melt adhesive than the second sheet layer;
sandwiching a plurality of elongated elastically stretchable members provided along a stretchable direction at intervals from each other between the first sheet layer and the second sheet layer; and
forming sheet bonded portions by bonding the first sheet layer and the second sheet layer via the hot melt adhesive disposed in a striped pattern that is intermittent in a longitudinal direction of the elastically stretchable members and continuously elongated in a direction intersecting with the elastically stretchable members;
wherein the low-adhesion nonwoven fabric of the first sheet layer has a higher area rate of concaves and a larger number of concaves per unit area than the nonwoven fabric of the second sheet layer.

12. A method of manufacturing the stretchable structure of an absorbent article, comprising:
using a first sheet layer and a second sheet layer, wherein the first sheet layer is made of a low-adhesion nonwoven fabric having a lower peel strength with respect to a hot melt adhesive than the second sheet layer;
sandwiching a plurality of elongated elastically stretchable members provided along a stretchable direction at intervals from each other between the first sheet layer and the second sheet layer; and
forming sheet bonded portions by bonding the first sheet layer and the second sheet layer via the hot melt adhesive disposed in a striped pattern that is intermittent in a longitudinal direction of the elastically stretchable members and continuously elongated in a direction intersecting with the elastically stretchable members;
wherein the low-adhesion nonwoven fabric of the first sheet layer has a higher content of a water repellent agent than the nonwoven fabric of the second sheet layer, or the water repellent agent is externally added to the low-adhesion nonwoven fabric of the first sheet layer and the water repellent agent is internally added to the nonwoven fabric of the second sheet layer.

13. A method of manufacturing the stretchable structure of an absorbent article, comprising:
- using a first sheet layer and a second sheet layer, wherein the first sheet layer is made of a low-adhesion nonwoven fabric having a lower peel strength with respect to a hot melt adhesive than the second sheet layer;
- sandwiching a plurality of elongated elastically stretchable members provided along a stretchable direction at intervals from each other between the first sheet layer and the second sheet layer; and
- forming sheet bonded portions by bonding the first sheet layer and the second sheet layer via the hot melt adhesive disposed in a striped pattern that is intermittent in a longitudinal direction of the elastically stretchable members and continuously elongated in a direction intersecting with the elastically stretchable members;
- wherein the low-adhesion nonwoven fabric of the first sheet layer has a higher content of a softening agent than the nonwoven fabric of the second sheet layer, or the softening agent is externally added to the low-adhesion nonwoven fabric of the first sheet layer, and the softening agent is internally added to the nonwoven fabric of the second sheet layer.

14. The stretchable structure of an absorbent article according to claim 2, wherein a width of each sheet bonded portion in the stretchable direction is 0.5 to 4 mm, and an interval between adjacent sheet bonded portions is 4 to 8 mm.

15. The method of manufacturing the stretchable structure of an absorbent article according to claim 8, comprising:
- a step of applying the hot melt adhesive, in which the second sheet layer is brought into contact with an engraved roll such that a circumferential direction of the engraved roll is a stretchable direction, and the hot melt adhesive, which is held in the striped pattern that is intermittent in the circumferential direction and continuous in an axial direction on the outer peripheral surface of the engraved roll, is transferred on the second sheet layer; and
- a step of performing pressure bonding, in which the elastically stretchable members are sandwiched between the first sheet layer and the second sheet layer on which the hot melt adhesive is transferred,
- wherein in the step of applying the hot melt adhesive, on the outer peripheral surface of the engraved roll, an application width in the circumferential direction of the hot melt adhesive is set to 0.5 to 4 mm, and an interval between the adjacent applications in the circumferential direction of the hot melt adhesive is set to 4 to 8 mm.

* * * * *